United States Patent
Shah

(10) Patent No.: US 9,017,734 B2
(45) Date of Patent: *Apr. 28, 2015

(54) PESTICIDAL COMPOSITION COMPRISING SULPHUR, AN INSECTICIDE AND AN AGROCHEMICAL EXCIPIENT

(76) Inventor: Deepak Pranjivandas Shah, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/981,617

(22) PCT Filed: Jan. 30, 2012

(86) PCT No.: PCT/IN2012/000066
§ 371 (c)(1),
(2), (4) Date: Jul. 25, 2013

(87) PCT Pub. No.: WO2012/101659
PCT Pub. Date: Aug. 2, 2012

(65) Prior Publication Data
US 2013/0302446 A1 Nov. 14, 2013

(30) Foreign Application Priority Data
Jan. 28, 2011 (IN) .......................... 251/MUM/2011

(51) Int. Cl.
*A01N 59/02* (2006.01)
*A01N 47/30* (2006.01)
*A01N 47/14* (2006.01)
*A01N 47/18* (2006.01)
*A01N 53/00* (2006.01)
*A01N 51/00* (2006.01)
*A01N 47/34* (2006.01)
*A01N 41/10* (2006.01)
*A01N 47/06* (2006.01)
*A01N 43/90* (2006.01)
*A01N 43/88* (2006.01)
*A01N 47/40* (2006.01)
*A01N 43/56* (2006.01)

(52) U.S. Cl.
CPC .............. *A01N 59/02* (2013.01); *A01N 41/10* (2013.01); *A01N 43/56* (2013.01); *A01N 43/88* (2013.01); *A01N 43/90* (2013.01); *A01N 47/06* (2013.01); *A01N 47/14* (2013.01); *A01N 47/18* (2013.01); *A01N 47/30* (2013.01); *A01N 47/34* (2013.01); *A01N 47/40* (2013.01); *A01N 51/00* (2013.01); *A01N 53/00* (2013.01)

(58) Field of Classification Search
None
See application file for complete search history.

(56) References Cited

U.S. PATENT DOCUMENTS 7,635,404 B1  12/2009  Devic et al.
2003/0124163 A1*  7/2003  de Vlieger .................... 424/405

FOREIGN PATENT DOCUMENTS

| CN | 101310582 A | 11/2008 |
| CN | 101857482 A | 10/2010 |
| CN | 101971854 A | 2/2011 |
| WO | 03/045877 A1 | 6/2003 |
| WO | 2004/026033 A1 | 4/2004 |
| WO | 2008/095913 A2 | 8/2008 |
| WO | WO 2010/095151 * | 8/2010 |

OTHER PUBLICATIONS

Ito, M. F., et al., "Acao Fungicida do Inseticida Cartap Sobre a Ferrugem do Feijoeiro. I—em Laboratorio", Fitopatol. Bras., 1996, 21, 44-49 p. 46, table 2.
Reddy, S. G. E., & Kumar, N. K. K., "Integrated Management of Two-Spotted Spider Mite, *Tetranychus urticae* (Koch) on Tomato Grown Under Polyhouse", Pest. Res. J., 2006, 18, 162-165 Abstract, col. 3-4.
Tomlin, C. D. S. (Ed.)., "The Pesticide Manual", 15th ed., 2009, BCPC:Hampshire, UK Entries 1, 5, 106, 130, 176, 213, 241, 377, 386, 485, 621, 691, 787, 801, 839, 840.
Sarmah, M., et al., "Bioefficacy of Insecticides in Combination with Acaricides and Nutrients Against *Helopeltis theivora* Waterhouse in Tea", Pest. Res. J., 2006, 18, 141-145 Whole document.

\* cited by examiner

Primary Examiner — Johann R Richter
Assistant Examiner — Katherine Peebles
(74) Attorney, Agent, or Firm — Wiley Rein LLP

(57) ABSTRACT

The present invention relates to an pesticidal composition comprising an effective amount of a sulphur; an effective amount of at least one insecticide selected from the group consisting of cartap fipronil, pirimicarb, buprofezine, thiachloprid, acetamiprid, clothianidin, diafenthiuron, novaluron, flubendiamide, spirotetramat, thiamethoxam, imidacloprid or salts thereof, and at least one agrochemically acceptable excipient.

9 Claims, No Drawings

PESTICIDAL COMPOSITION COMPRISING SULPHUR, AN INSECTICIDE AND AN AGROCHEMICAL EXCIPIENT

BACKGROUND OF THE INVENTION

1. Field of the Invention

The present invention relates to a pesticidal composition comprising an effective amount of sulphur; an effective amount of at least one insecticide or salt thereof, and at least one agrochemically acceptable excipient. The invention further relates to a method of application of the pesticidal composition to crops.

2. Description of the Related Art

The role of elemental sulphur as a pesticide has been known for a long time. The role of sulphur in controlling, inhibiting and eradicating the growth of fungi such as mildews is well known. Sulphur is mostly available in its elemental form and different formulations such as granules, pellets, powders, etc. are known for providing sulphur in a form for use as a fertilizer or pesticide. Sulphur formulations used alone are good to moderately effective against powdery mildew and mites. They are also used as clean up applications for hibernating mite populations before the onset of plant protection schedules in horticultural and perennial crops like tea. Sulphur not only works as a acaricide, for example on powdery mildew but is also used as a supplementary plant nutrient and fungicide.

Further demands on insecticidal and acaricidal compounds include reduced phytotoxicity, reduced dosage, substantial broadening of spectrum and increased safety, to name a few.

The biological properties of known compounds are not entirely satisfactory in the areas of pest control, phytotoxicity, and environmental and worker exposure, for example. In particular, it has been observed that the pests show resistance to the pesticide, which are at times administered in higher dosages to achieve the desired control, thereby leading to soil toxicity and other environmental hazards, besides higher costs.

Hence, there is a need to develop a composition which addresses the problem of resistance and soil toxicity and also is used at reduced dosages, controls environmental damage, offers broader crop protection spectrum, improved and healthy foliage, rainfastness, improved crop yield, saves labour, better grain quality and management against various insects and pests, improves plant growth, and is yet cost-effective to the end user.

SUMMARY OF THE INVENTION

It has now been discovered that a pesticidal composition comprising an effective amount of a sulphur, an effective amount of at least one insecticide selected from the group consisting of cartap fipronil, pirimicarb, buprofezine, thiachloprid, acetamiprid, clothianidin, diafenthiuron, novaluron, flubendiamide, spirotetramat, thiamethoxam, imidacloprid or salts thereof and at least one agrochemically acceptable demonstrated excellent efficacy against various pests and mites for example, Lepidoptera, various sucking pests, termites etc.

Surprisingly, the inventors of the application have discovered that a pesticidal composition comprising sulphur in the range from 32.5% to 90%, abamectin in the range from 0.08% to 3.6% and its salts thereof and at least one agrochemically acceptable excipient demonstrates surprisingly excellent efficacy for example, against red spider mites and leaf minor.

Surprisingly, the inventors of the application have also discovered that the pesticidal composition comprising sulphur in the range from 30% to 90%, lambda-cyhalothrin in the range from 0.35% to 4% or its salts thereof and at least one agrochemically acceptable excipient was highly efficacious against the pests and the mite populations.

The pesticidal compositions offers a broad spectrum of protection, addresses the concerns of resistance, improves foliage, improves rainfastedness and in various instances, improves crop yield and grain quality. The compositions disclosed herein, also serve as an intervention application between very specific actives, which alone are likely to lead to resistance in areas of epidemic and high frequency of pesticidal application.

Quite advantageously, in certain cases, the compositions can be applied as a foliar spray or to the soil, through broadcasting or through drip or trickle irrigation. The latter case of drip or trickle irrigation further optimizes farming practices, which are greatly challenged by an ever-increasing labour and water shortage. In some cases, it has been observed, that the compositions at very low concentrations of the active ingredients can be effectively applied, thereby reducing the burden on the environment. In certain cases, it has also been noted that the compositions at lower rates of the active ingredients in combination together provided a longer duration of control of the pest and avoided pest outbreak and resurgence.

DETAILED DESCRIPTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The present invention relates to a pesticidal composition comprising an effective amount of sulphur, an effective amount of at least one insecticide selected from the group consisting of cartap fipronil, pirimicarb, buprofezine, thiachloprid, acetamiprid, clothianidin, diafenthiuron, novaluron, flubendiamide, spirotetramat, thiamethoxam, imidacloprid or salts thereof and at least one agrochemically acceptable excipient.

According to an embodiment, sulphur is present in a range from 20% to 90% of the weight of the composition. According to an embodiment the insecticide is present in a range from 0.1% to 40% of the weight of the composition.

The pesticidal composition can be in a solid form or a liquid form or a gel. For example, the pesticidal composition may be in the form of emulsion concentrates, wettable powders, suspension concentrates, suspo emulsions, microemulsions, capsulated suspension, water dispersible granules, pellets, seed dressings or emulsions for seed treatment, broadcast granules, gel, emulsions in water, oil dispersions, etc.

Preferably, the pesticidal composition is in the form of water dispersible granules. When the composition is the in the form of water dispersible granules, usually, sulphur is present in the range of 40% to 90% and the insecticide is usually present in the range of 0.1% to 40% of the total composition.

Preferably, the pesticidal composition is in the form of suspension concentrates. When the composition is in the form suspension concentrates, usually, sulphur is present in the range of 20% to 70% and the insecticide is present in the range from 0.25% to 17.5% of the total composition.

Water dispersible granules can be defined as a pesticide formulation consisting of granules to be applied after disintegration and dispersion in water. As described herein, "WG" or "WDG" refer to water dispersible granules.

Suspension concentrate can be defined as a stable suspension of solid pesticides in a fluid usually intended for dilution with water before use. As described herein, "SC" refers to suspension concentrates.

As defined herein, WP refers to a wettable powder, which can be a powder formulation to be applied as a suspension after dispersion in water. As defined herein, EC refers to an emulsifiable concentrate, which can be a liquid homogenous formulation to be applied as an emulsion after dilution in water. As described herein, OD refers to an oil dispersion which is a stable suspension of active ingredient(s) in a water-immiscible fluid, which may contain other dissolved active ingredients(s), intended for dilution with water before use. As described herein, ZC refers to a stable suspension of capsules and active ingredient, in fluid, normally intended for dilution with water before use. As described herein, gel refers to a sol in which the solid particles are meshed such that a rigid or semi-rigid mixture results. As described herein, CS refers to capsulated suspension which is a stable suspension of microencapsulated active ingredient in an aqueous continuous phase, intended for dilution with water before use. As described herein, SE refers to Suspo Emulsion, which is a fluid heterogenous formulation consisting of active ingredients in the form of solid particles and fine globules in continuous water phase.

As described herein, the abbreviation "DAS" refers to Days After Spraying. As described herein, the abbreviation "DAT" refers to Days after Transplanting. As described herein, the abbreviation "DAP" refers to Days after Planting.

According to an embodiment, the composition comprises sulphur is in the range form 50% to 90% and cartap hydrochloride in the range from 2.25% to 15% of the total weight of the composition.

According to another embodiment, the composition comprising sulphur and cartap hydrochloride is in the form of wettable powder or broadcast granules which are water dispersible.

According to an embodiment, sulphur is in the range from 40% to 90% and fipronil in the range from 0.3% to 10% of the total weight of the composition. According to another embodiment, sulphur is in the range from 80% to 90% and fipronil is in the range from 0.3% to 10% of the total weight of the composition in the form of water dispersible granules. According to still another embodiment, sulphur is in the range from 40% to 70% and fipronil is in the range of 0.3% to 10% of the total composition in the form of suspension concentrate. According to yet another embodiment, sulphur is in the range from 60% to 90% and fipronil is in the range of 0.3% to 1% of the total composition in the form of broadcast granules which are water dispersible.

Broadcast granules which include sulphur and cartap hydrochloride or sulphur and fipronil, may be applied to the soil by broadcasting or through trickle or drip irrigation to effectively reach the roots of desired crops.

According to an embodiment, sulphur is in the range from 30% to 75% and pirimicarb in the range from 2.5% to 9% of the total weight of the composition. According to another embodiment, sulphur is in the range from 60% to 75% and pirimicarb is in the range from 5% to 9% of the total weight of the composition in the form of water dispersible granules. According to still another embodiment, sulphur is in the range from 30% to 70% and pirimicarb is in the range from 2.5% to 3% of the total weight of the composition in the form of suspension concentrate.

According to an embodiment, sulphur is in the range from 30% to 75% and buprofezine in the range from 5% to 25% of the total weight of the composition. According to another embodiment, sulphur is in the range from 40% to 75% and buprofezin is in the range from 10% to 20% of the total weight of the composition in the form of water dispersible granules. According to another embodiment, sulphur is in the range from 30% to 70% and buprofezine is in the range from 5% to 10% of the total weight of the composition in the form of suspension concentrate.

According to an embodiment, sulphur is in the range from 30% to 80% and thiacloprid in the range from 3% to 10% of the total weight of the composition. According to another embodiment, sulphur is in the range from 60% to 80% and thiacloprid is in the range from 6% to 10% of the total weight of the composition in the form of water dispersible granules. According to another embodiment, sulphur is in the range from 30% to 70% and thiacloprid is in the range from 3% to 10% of the total weight of the composition in the form of suspension concentrate.

According to an embodiment, sulphur is in the range from 35% to 80% and acetamiprid in the range from 0.5% to 5% of the total weight of the composition. According to another embodiment, sulphur is in the range from 50% to 80% and acetamiprid is in the range from 0.5% to 3% of the total weight of the composition in the form of water dispersible granules or water soluble granules or wettable powders.

According to an embodiment, sulphur is in the range from 25% to 80% and clothianidin in the range from 0.25% to 3% of the total weight of the composition. According to an embodiment, sulphur is in the range from 50% to 80% and clothianidin is in the range of 0.5% to 3% of the total weight of the composition in the form of water dispersible granules. According to an embodiment, sulphur is in the range from 30% to 70% and clothianidin is in the range of 0.25% to 1.5% of the total weight of the composition in the form of suspension concentrate.

According to an embodiment, sulphur is in the range from 20% to 75% and diafenthiuron in the range from 7.5% to 50% of the total weight of the composition. According to another embodiment, sulphur is in the range from 40% to 75% and diafenthiuron is in the range from 12% to 40% of the total weight of the composition in the form of water dispersible granules. According to another embodiment, sulphur is in the range from 30% to 70% and diafenthiuron is in the range from 7.5% to 17.5% of the total weight of the composition in the form of suspension concentrate.

According to an embodiment, sulphur is in the range from 35% to 80% and novaluron in the range from 1.25% to 10% of the total weight of the composition. According to an embodiment, sulphur is in the range from 70% to 80% and novaluron is in the range of 2.5% to 10% of the total weight of the composition in the form of water dispersible granules. According to an embodiment, sulphur is in the range from 35% to 70% and novaluron is in the range from 1.25% to 4% of the total weight of the composition in the form of suspension concentrate.

According to an embodiment, sulphur is in the range from 25% to 80% and flubendiamide in the range from 1% to 6% of the total weight of the composition. According to an embodiment, sulphur is in the range from 60% to 80% and flubendiamide is in the range from 1% to 6% of the total weight of the composition in the form of water dispersible granules. According to an embodiment, sulphur is in the range from 25% to 70% and flubendiamide is in the range from 1% to 4% of the total weight of the composition in the form of suspension concentrate.

According to an embodiment, sulphur is in the range from 25% to 80% and spirotetramat in the range from 2% to 13% of the total weight of the composition. According to an embodiment, sulphur is in the range from 50% to 80% and spirotetramat is in the range from 3% to 13% of the total weight of the composition in the form of water dispersible granules. According to an embodiment, sulphur is in the range from 25% to 70% and spirotetramat is in the range from 2% to 10% of the total weight of the composition in the form of suspension concentrate.

According to an embodiment, sulphur is in the range from 25% to 80% and thiamethoxam in the range from 0.67% to 5% of the total weight of the composition. According to another embodiment, sulphur is in the range from 50% to 80% and thiamethoxam is in the range from 1.5% to 10% of the total weight of the composition in the form of water dispersible granules or water soluble granules or wettable powders. According to another embodiment, sulphur is in the range from 25% to 70% and thiamethoxam is in the range from 0.67% to 5% of the total weight of the composition in the form of suspension concentrates.

According to an embodiment, sulphur is in the range from 25% to 90% and imidacloprid in the range from 0.1% to 4% of the total weight of the composition. According to another embodiment, sulphur is in the range from 50% to 80% and imidacloprid in the range from 0.1% to 4% of the total weight of the composition in the form of water dispersible granules. According to another embodiment, sulphur is in the range from 25% to 70% and imidacloprid is in the range from 0.1% to 4% of the total weight of the composition in the form of suspension concentrates. According to yet another embodiment, sulphur is in the range from 50% to 90% and imidacloprid is in the range from 0.1% to 4% of the total weight of the composition in the form of granules for broadcast application.

According to an embodiment, the compositions comprising sulphur and imidacloprid can also be in the form of a gel.

The invention further relates to a pesticidal composition comprising sulphur in the range from 32.5% to 90%, abamectin in the range from 0.08% to 3.6% of the total weight of the composition and at least one agrochemically acceptable excipient. According to an embodiment, sulphur is in the range from 65% to 90% and abamectin is in the range from 0.08% to 3.6% of the total weight of the composition in the form of water dispersible granules. According to another embodiment, sulphur is in the range from 32.5% to 70% and abamectin is in the range from 0.75% to 3.6% of the total weight of the composition in the form of suspension concentrate.

The invention further relates to a pesticidal composition comprising sulphur in the range from 40% to 90%, lambda-cyhalothrin in the range from 0.5% to 5% of the total weight of the composition, and at least one agrochemically acceptable excipient.

According to an embodiment, the composition comprising sulphur and lambda cyhalothrin is in the form of wettable powder. According to an embodiment, the composition comprising sulphur and lambda cyhalothrin can be in the form of a ZC. According to yet another embodiment, the composition comprising sulphur and lambda-cyhalothrin can be in the form of a gel.

According to yet another embodiment, the at least one agrochemically acceptable excipient can comprise wetting agents, dispersing agents, emulsifiers binding agents, sticking agents, fillers, diluents, solvents, coating agents and stabilizers. However, those skilled in the art will appreciate that it is possible to utilize additional agrochemically acceptable excipients without departing from the scope of the present invention. The agrochemically acceptable excipient is in the range from 7% to 80% of the total weight of the composition.

Wetting agents which can be commonly used include sulfosuccinates, naphthalene sulfonates, sulfated esters, phosphate esters, sulfated alcohol and alkyl benzene sulfonates. However, those skilled in the art will appreciate that it is possible to utilize other wetting agents known in the art without departing from the scope of the invention.

Dispersing agents which can be commonly used include polycarboxylates, naphthalene sulfonate condensates, phenol sulfonic acid condensates, lignosulfonates, methyl oleyl taurates and polyvinyl alcohols. However, those skilled in the art will appreciate that it is possible to utilize other dispersing agents known in the art without departing from the scope of the invention.

Emulsifiers can be of the anionic, cationic or non-ionic type. Emulsifiers which do not cause the liquid active substance to solidify are particularly preferred. Some liquid actives are completely miscible in water and may not require an emulsifier. These emulsifiers are usually used in admixture. The emulsifiers which are commonly used include ethoxylated and ethopropoxylated alcohols and nonyl phenols, ethoxylated tristeryl phenol, ethoxylated tristeryl phenol phosphates, ethoxylated and ethopropoxylated castor oil, calcium alkyl benzene sulfonates and proprietary blended emulsifiers. However, those skilled in the art will appreciate that it is possible to utilize other emulsifiers known in the art without departing from the scope of the invention.

Fillers which can be commonly used include diatomaceous earth, kaolin, bentonite, precipitated silica, attapulgite, and perlite. However, those skilled in the art will appreciate that it is possible to utilize other emulsifiers known in the art without departing from the scope of the invention.

Diluents which can be commonly used include one or more of tone calcite, mica, soap powder, dolomite and lactose. However, those skilled in the art will appreciate that it is possible to utilize other diluents known in the art without departing from the scope of the invention.

Solvents which can be commonly used include one or more of N,N-dimethyl decanamide, N-methyl pyrrolidone, cyclohexanone, dimethyl formamide, tetrahydrofuran, dimethylsulfoxide, petroleum distillates and chlorobenzenes. However, those skilled in the art will appreciate that it is possible to utilize other solvents known in the art without departing from the scope of the invention.

The compositions comprising sulphur and an insecticide can be prepared by various processes.

Water dispersible granule compositions can be made by various processes such as spray drying, fluid bed spray granulation, extrusion, pan granulation, etc. One way of making water dispersible granular compositions which include sulphur and the insecticide, involves initially blending required additives such as wetting agents, dispersing agents, emulsifiers, solvents, fillers to obtain an additive mix. The additive mix obtained is dispersed in sufficient quantity of water to form a blend. A requisite amount of insecticide technical and sulphur technical are slowly added to the blend by high shear mixing. Further agrochemically acceptable excipients such as fillers can be added, if required to form a mixture. The above mixture is wet milled using a bead mill to obtain an average particle size of less than 50 microns, preferably less than 15 microns, preferably 1 to 10 microns to obtain the mill base. The mill base is granulated in an appropriate spray drier or other drying methods with an outlet of a suitable temperature followed by sieving to remove the under sized and oversized granules, to obtain a WG formulation comprising sulphur and insecticide in combination.

Alternately stable aqueous suspension concentrates compositions of sulphur and the insecticide may be prepared by blending required additives such as wetting agents, dispersing agents, emulsifiers, fillers to obtain an additive mix. Then a mill base having an average particle size of less than 50 microns, preferably less than 15 microns, preferably 1 to 10 microns is prepared by milling a mixture of requisite amount of the insecticide and sulphur technical in appropriate ratios in additive mix in required amount of water containing solvent. Further, sufficient quantity of water with required amounts of binders and preservatives is added to the mill base and mixed thoroughly to get the SC formulations of the desired combination of sulphur and the insecticide.

Alternately, wettable powder compositions of sulphur and a solid insecticide can be prepared by blending required additives such as wetting agents, dispersing agents, emulsifiers, fillers to obtain an additive mix. Further essential amount of sulphur and insecticide technical are blended thoroughly with appropriate weight of additive mix, carrier and the required amount of filler. The mixture is then micronised using a suitable mill like fluid energy mill, jet mill, pin mill, hammer mill to an average particle size of less than 50 microns, preferably less than 15 microns, preferably 4 to 10 microns to get the WP formulation comprising sulphur and insecticide in combination.

The wettable powder compositions of sulphur and liquid insecticide can be prepared by blending required additives such as wetting agents, dispersing agents, emulsifiers, fillers to obtain an additive mix. An essential quantity of sulphur technical, additive mix and optionally a filler are blended together and are then micronised using a suitable mill like fluid energy mill to an average particle size of less than 50 microns, preferably less than 15 microns, preferably 4 to 10 microns to obtain a sulphur base. The requisite amount of liquid pesticide is then absorbed on to carrier to obtain an insecticide base. The proportionate amount of the insecticide base and the sulphur base are blended thoroughly to get the WP formulation.

Alternatively, emulsifiable concentrate (EC) compositions can be prepared by dissolving required quantity of the insecticide in a solvent to obtain a solution. A blend of non ionic and an anionic emulsifier are added to the solution to obtain the EC of the insecticide.

The compositions of the invention can also be in the form of a ZC which can be prepared by initially preparing a suspension concentrate (SC) of a first active and a capsulated suspension (CS) of a second active, and then mixing the SC and CS. The SC can be prepared by methods described earlier in the application. CS formulation of the insecticide is prepared separately by emulsifying the required amount of liquid or molten insecticide with or without a solvent along with requisite amount additives such as monomers, emulsifiers, dispersing agents at ambient or elevated temperature with or without catalysts.

Alternatively, compositions comprising sulphur and insecticides in the form of a gel can be prepared by mixing the required quantity of sulphur suspension as prepared above with additives like feed stimulants such as dextrose along with requisite amounts of attractants, flavours, feed stimulants, gelling agents and activators for gelling.

According to an embodiment, the invention relates to a method of application of an effective amount of the pesticidal composition, wherein the composition is applied to crops through foliar spray or soil application or through drip irrigation or trickle irrigation.

Through the agrochemical compositions, it has been observed that the number of applications to control wide range of pests appearing at the same time is minimized. The compositions are highly safe to the user and to the environment. The compositions are also cost-effective, as they provide much greater simultaneous control and can be used in a variety of crops with a broader spectrum of protection improved and healthy foliage, rainfastedness, improved crop yield, better grain quality. The pesticidal compositions in practice also serve the purpose of simultaneously managing the damage caused by termites found in same medium (soil) and meeting the need of sulphur fertilizer required in the initial stages of plant growth. The compositions are thereby rendered highly economical and beneficial to the end-users when compared to the standalone compositions of the insecticide and sulphur. Also, the compositions serve as an intervention application between very specific actives likely to lead to resistance in areas of epidemic and high frequency of pesticidal applications.

EXAMPLES

Example 1

Sulphur 65%+Buprofezin 14% WG

Step 1: Preparation of 'Additive Mix'

25 parts of Sodium salt of naphthalene sulfonate condensate (eg. Tamol NN 8906), 25 parts of Sodium salt of phenol sulfonate condensate (eg. Tamol PP), 100 parts of Sodium lignin sulfonate (eg. Reax 100M) and 50 parts of Kaolin (eg. Barden clay) are blended together and used as 'additive mix'.

Step 2: Preparation of Mill Base 18 parts of 'additive mix' is first dispersed in 100 parts of water. Added slowly 15 parts of Buprofezin technical (95% purity) and 67 parts of sulphur technical (99% purity) under high shear mixing. The mixture is wet milled using a bead mill to an average particle size of around 2 microns to get the mill base.

Step 3: Spray Granulation of Mill Base

The above mill base is spray granulated in an appropriate spray drier with an out let temperature around 70 degree C. followed by sieving to remove the under sized and oversized, to get Sulphur 65%+Buprofezin 14% WG.

Example 2

Sulphur 50%+Diafenthiuron 35% WG

Mill base prepared by milling a mixture of 36 parts of Difenthiuron technical (95% purity), 51.5 parts of sulphur technical (99% purity), 12.5 parts of 'additive mix' in 100 parts of water is spray granulated as in Example 1 to get Sulphur 50%+Difenthiuron 35% WG.

Example 3

Sulphur 85%+Fipronil 0.4% WG

Mill base prepared by milling a mixture of 0.5 part of Fipronil technical (96% purity), 87 parts of sulphur technical (99% purity), 12.5 parts of 'additive mix' in 100 parts of water is spray granulated as in Example 1 to get Sulphur 85%+Fipronil 0.4% WG.

Example 4

Sulphur 40%+Thiamethoxam 2% SC

Mill base, having an average particle size of around 2 microns, is prepared as in Example 1 by milling a mixture of 2.3 parts of Thiamethoxam (98% purity), 41.5 parts of sulphur technical (99% purity), 10 parts of 'additive mix' in 37.7 parts of water containing 5 parts of propylene glycol. 8.5 parts of 2% dispersion of xanthum gum (eg. Rhodopol) in water containing 0.5% 1,2-Benzisothiazolin-3-one (eg. Proxel) is then added to the mill base and mixed thoroughly to get Sulphur 40%+Thiamethoxam 2% SC.

Example 5

Sulphur+Cartap (WP)

Sulphur and cartap Hydrochloride are micronized by suitable milling equipment, below 75 microns, preferably below 15 microns, and the micronized powder of the active ingredients thus obtained can be blended in a closed environment with the excipients in the right proportions to achieve the desired composition. The blended actives and excipients can also be compacted through a compactor, a pelletizer or pastillator or pan granulated to form granules.

Efficacy Trials:

The efficacy trials conducted using stand-alone treatments of sulphur and the insecticides were done in accordance with the standard recommended dosages for these active ingredients in India. However, it may be noted that the recommended dosages for each active ingredient may vary as per recommendations in a particular country, soil conditions, weather conditions and disease incidence.

Example 1

Bioefficacy of Sulphur+Cartap Granules

The trials were conducted in Karnal district of Haryana state in India on paddy, to evaluate the effectiveness of sulphur plus cartap granules in various combinations. The experiments were also conducted using Sulphur 90% WG standalone and Cartap Hydrochloride 4% Granules standalone used as standards for comparison as well as an untreated control. The treatments were carried out following the randomized block design and keeping all the agronomic practices uniform for all the treatments. It is to be noted that the larvae of *Scirpophaga incertulas* Walker cause dead hearts during vegetative stage and white ear heads during reproductive stage. Even though rice plant can compensate if dead heart infestation does not exceed 10 percent, it cannot compensate for the white ear loss.

The treatments were carried out by broadcasting the compositions twice the on $30^{th}$ and the $60^{th}$ days after transplanting of the paddy. Both the applications and their efficacy were evaluated. To avoid intermixing of treatments, about 20 to 30 cm thick false bund boundaries were prepared all around plots having the treatments of granular insecticides.

The treatments applied were as indicated in the table below:

TABLE 1A

| Treatments | Compositions | Active ingredient (grams/hectare) | Formulation dosage in gm/ha | Percent dead heart per hill 50 DAT | Percent dead heart per hill 75 DAT | White ear head (%) |
|---|---|---|---|---|---|---|
| 1 | Sulphur 90% + Cartap 2.25% WP | 13500 + 337 | 15000 | 3.20 | 3.68 | 5.31 |
| 2 | Sulphur 70% + Cartap Hydrochloride 4% WP | 10500 + 600 | 15000 | 2.70 | 2.37 | 3.5 |
| 3 | Sulphur 60% + Cartap Hydrochloride 6% WP | 9000 + 900 | 15000 | 2.48 | 2.15 | 3.24 |
| 4 | Sulphur 50% + Cartap Hydrochloride 7.5% WP | 7500 + 1125 | 20000 | 3.15 | 2.86 | 4.62 |
| 5 | Sulphur 90% WG | 6750 | 7500 | 6.86 | 5.42 | 10.54 |
| 6 | Cartap Hyrochloride 4% Granules | 750 | 18750 | 2.21 | 2.42 | 3.23 |
| 7 | Untreated check | — | — | 12 | 10.64 | 14.36 |

It was noted that the application of Sulphur 60%+Cartap Hydrochloride 6% WP at 9000+900 g.a.i. per hectare (Treatment 3) provided better control over the population of stem borer at 75 days after transplanting in comparison to cartap (Treatment 6).

Apart from controlling the larvae of *Scirpophaga incertulas*, the combined product of sulphur+Cartap Hydrochloride in varying concentrations also displayed a valuable impact on the physiological factors like improved foliage (greenness) in paddy and an increase in the number of tillers, contributing to higher yield.

Below is a tabular presentation of the yield indicating the number of tillers at 60 DAT (days after transplanting)

TABLE 1B

| Treatment | Composition | Active ingredient (grams/hectare) | Number of tillers (Mean of randomly selected 5 plants) |
|---|---|---|---|
| 1 | Sulphur 90% + Cartap Hydrochloride 2.25% WP | 13500 + 337 | 6.95 |
| 2 | Sulphur 70% + Cartap hydrochloride 4% WP | 10500 + 600 | 6.46 |
| 3 | Sulphur 60% + Cartap Hydrochloride 6% WP | 9000 + 900 | 6.27 |
| 4 | Sulphur 50% + Cartap Hydrochloride 7.5% WP | 7500 + 1125 | 5.78 |
| 5 | Sulphur 90% WG | 6750 | 5.27 |
| 6 | Cartap Hydrochloride 4% Granules | 750 | 4.78 |

The maximum numbers of tillers were observed with the application of Sulphur 90%+Cartap Hydrochloride 2.25% WP at 13500+337 g.a.i. per hectare (Treatment 1). The application of Sulphur 70%+cartap hydrochloride 4% WP at 10500+600 g.a.i. per hectare (Treatment 2) also showed a significant increase in the number of tillers observed.

This increase in the number of tillers as compared to the individual application of Cartap hydrochloride 4% Granules (Treatment 6) is due to the presence of sulphur in the composition. The crops also exhibited enhanced chlorophyll content due to the application of sulphur in combination with cartap in varying concentrations.

The above composition in practice serves the purpose of simultaneously managing the damage caused by stem borer and the need of sulphur fertilizer required in the initial stages of plant growth, thereby rendering the composition more economical and beneficial to the end-users when compared to the individual application of Cartap or Sulphur.

The above composition also restricts the undue loading of a carrier such as sand which is present upto the extent of 90% in standalone Cartap composition which is actually a waste.

Example 2A

Bioefficacy of Sulphur+Fipronil WG

The treatments were carried out during kharif in Akola district of Maharashtra in India on cotton in a plot size of 5.4×5.4 sq.m with a spacing of 90×60 cm. The experiments were configured with nine treatments which were replicated four times. The crop was raised following all standard agronomical practices in a randomized block design condition. The treatments were imposed as and when a significant number of sucking pests such as nymphs of jassids, nymphs/adults of thrips or aphids per leaf were observed. All the agronomic practices were adopted as per recommendations.

The populations of sucking pests viz., thrips, aphids and leafhoppers were recorded from randomly selected ten plants. A day before the imposition of treatment, the populations of sucking pest were found to be quite uniform and above the economic threshold level.

The below table shows the details of the treatments applied and the pest population after the 5$^{th}$ day of spraying.

TABLE 2A

| Treatments | Compositions | Active ingredients (grams/hectare) | Formulation Dosage in grams/hectare | Day Before spray | No. of thrips/3 leaves | No. of Jassid/3 leaves | No. of Aphids/3 leaves | No. of mites/3 leaves | No. of Predator/plant |
|---|---|---|---|---|---|---|---|---|---|
| 1 | Sulphur 85% + Fipronil 10% WG | 1275 + 150 | 1500 | 43 | 9 | 12 | 1 | 2 | 3 |
| 2 | Sulphur 85% + Fipronil 7% WG | 1275 + 105 | 1500 | 40 | 7 | 16 | 3 | 4 | 3 |
| 3 | Sulphur 80% + Fipronil 6% WG | 1200 + 90 | 1500 | 41 | 9 | 19 | 7 | 7 | 3 |
| 4 | Sulphur (80%) + Fipronil (5%) WG | 1200 + 75 | 1500 | 45 | 13 | 22 | 8 | 7 | 2 |
| 5 | Sulphur 42.5% + Fipronil 3.5% SC | 637.5 + 52.5 | 1500 | 43 | 10 | 19 | 7 | 5 | 2 |
| 6 | Sulphur 40% + Fipronil 2.5% SC | 600 + 37.5 | 1500 | 49 | 19 | 27 | 10 | 8 | 3 |
| 7 | Sulphur 80% WG | 1200 | 1500 | 45 | 34 | 38 | 29 | 8 | 2 |
| 8 | Fipronil 5% SC | 80 | 1500 | 42 | 14 | 21 | 5 | 17 | 2 |
| 9 | Untreated check | — | | 45 | 48 | 51 | 50 | 49 | 3 |

It was observed that the application of Sulphur 85%+Fipronil 10% WG at 1275+150 g.a.i per hectare (Treatment 1) was highly effective in controlling the sucking pest.

The application of Sulphur 85%+Fipronil 7% WG at 1275+105 g.a.i per hectare (Treatment 2) was found effective in controlling the pest as compared to individual application of Sulphur 80% WG (Treatment 7) and Fipronil 5% SC (Treatment 8).

It was also noticed that the SC formulation Sulphur 42.5%+Fipronil 3.5% SC at 637.5+52.5 g.a.i per hectare (Treatment 5) showed a good efficacy over the population of thrips, mites, jassid and aphids and better control of the pest population for a longer period of time as compared to Treatment 7 and Treatment 8 with the individual actives at higher concentrations.

Example 2B

Bioefficacy of Sulphur+Fipronil Granule

The treatments were conducted in Lucknow district of Uttar Pradesh State in India on sugarcane following a randomized block treatment with seven treatments and four replications. Each treatment had 25 suckers planted in a row and the whole application of all the treatments was carried out on the 35$^{th}$ and 65$^{th}$ day after planting. All the agronomic practices were adopted as per recommendations.

The treatments included combinations of Sulphur+fipronil with varying concentration of the active ingredients, Sulphur 80% WG stand alone and Fipronil 0.3% granules stand alone use as standards for comparison along with an untreated control were evaluated against sugarcane shoot borer, *Chilo infuscatellus* Snellen and root borer. *Emmalocera depressella* Swinhoe. The treatments were applied as indicated in the table below

TABLE 2B

| Treatments | Composition | Active ingredients (grams/hectare) | Formulation Dosage in grams/hectare | Mean percentage of affected plants with shoot borer and root borer (randomly selected 25 plant) | Yield (ton/ha) |
|---|---|---|---|---|---|
| 1 | Sulphur 90% + Fipronil 0.3 | 13500 + 45 | 15000 | 3.78 | 95 |
| 2 | Sulphur 80% + Fipronil 0.5% Granules. | 12000 + 75 | 15000 | 2.57 | 98 |
| 3 | Sulphur 70% + Fipronil 0.7% Granules. | 10500 + 105 | 15000 | 1.85 | 101 |
| 4 | Sulphur 60% + Fipronil 1% Granules. | 9000 + 150 | 15000 | 1.32 | 103 |
| 5 | Sulphur 90% WG | 6750 | 7500 | 8.59 | 95 |
| 6 | Fipronil 0.3% Granules | 100 | 25000 | 3.6 | 98 |
| 7 | Untreated check | — | — | 14.57 | 70 |

It was observed that the application of Sulphur 70%+Fipronil 0.7% Granules at 10500+105 g.a.i per hectare (Treatment 3) and Sulphur 60%+Fipronil 1% Granules. at 9000+150 g.a.i per hectare (Treatment 4) were found superior in controlling the shoot borer and root borer population as compared to individual application of Sulphur 90% WG (Treatment 5) and Fipronil 0.3% Granules (Treatment 6).

The physiological and nutritional behavior of sulphur were also evaluated and noticed by randomly selecting 25 cane plant and counting the nodes/internodes and the circumference of the cane to know the thickness of cane as illustrated in the Table below:

TABLE 2C

| Treatments | Composition | Active ingredients (grams/hectare) | Formulation Dosage in grams/hectare | Number of internodes per cane (mean of 25 randomly selected cane) | Thickness of cane (in cm). (mean of 25 randomly selected canes) |
|---|---|---|---|---|---|
| 1 | Sulphur 90% + Fipronil 0.3% | 13500 + 45 | 15000 | 14.75 | 17.27 |
| 2 | Sulphur 80% + Fipronil 0.5% Granules. | 12000 + 75 | 15000 | 13.47 | 17.03 |
| 3 | Sulphur 70% + Fipronil 0.7% Granules. | 10500 + 105 | 15000 | 13.26 | 16.69 |

TABLE 2C-continued

| Treatments | Composition | Active ingredients (grams/hectare) | Formulation Dosage in grams/hectare | Number of internodes per cane (mean of 25 randomly selected cane) | Thickness of cane (in cm). (mean of 25 randomly selected canes) |
|---|---|---|---|---|---|
| 4 | Sulphur 60% + Fipronil 1% Granules. | 9000 + 150 | 15000 | 13.22 | 16.44 |
| 5 | Sulphur 50 + Fipronil 1.2% Granules. | 7500 + 180 | 15000 | 12.73 | 15.78 |
| 6 | Sulphur 90% WG | 6750 | 7500 | 8.59 | 14 |
| 7 | Fipronil 0.3% Granule | 100 | 25000 | 7.00 | 13.5 |
| 8 | Untreated check | — | — | 12.46 | 15.32 |

It was also observed that applications of fipronil and sulphur in combination not only provided good control over the pest population but also significantly increased the yield which was noted in terms of thickness and girth of the cane and an increase in the height as well as the length internodes of sugarcane as compared to the individual treatment with fipronil used alone.

The above composition serves a dual purpose of simultaneously managing the damage caused by shoot borer and meeting the fertilizer requirement in the initial stages of plant growth with the presence of sulphur in the composition. The composition is thereby more economical and beneficial to the end-users when compared with the present practices of solo application of fipronil granules and sulphur fertilizer that saves not only the additional labour but also the vital cost of solo Sulphur fertilizer.

The above composition also restricts the undue loading of a carrier such as sand which is present upto the extent of 90% in standalone Fipronil Granule composition.

Example 3

Bioefficacy for Sulphur+Pirimicarb

The field trials were carried out in the Rajkot district of Gujarat state in India on cotton following a randomized block design with four replications and eight treatments with a plot size of 3.6×6.0 m. The varieties viz., Bt cotton, CV Vikram-5, were transplanted in experimental fields. All the agronomic practices were adopted as per recommendations.

The treatments included combinations of Sulphur plus Pirimicarb with varying concentration of the active ingredients, Sulphur 80% WG stand alone and Pirimicarb 50% WG stand alone used as standards for comparison along with an untreated control.

The treatments were carried out after the development of sufficient population of aphid and mites on plants after 20-25 days of transplanting. Five plants were selected randomly in each plot and tagged. On each plant, three twigs selected randomly were observed critically for the mites and the number of aphids and mites were counted before as well as after the $3^{rd}$, $7^{th}$, $10^{th}$ and $15^{th}$ days of each spraying.

The treatments were applied were as indicated in the table below:

TABLE 3

| Treatment | Composition | Active ingredients (grams/hectare) | Formulation Dosage in grams/hectare | Average no. of aphids/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 60% + Pirimicarb 13% WDG | 900 + 200 | 1500 | 68 | 20 | 3 | 0 | 0 | 55 | 13 | 6 | 0 | 0 |
| 2 | Sulphur 70% + Pirimicarb 9% WDG | 1050 + 135 | 1500 | 72 | 25 | 7 | 2 | 0 | 69 | 18 | 8 | 3 | 0 |
| 3 | Sulphur 75% + Pirimicarb 5% WDG | 1125 + 75 | 1500 | 60 | 28 | 18 | 12 | 11 | 49 | 12 | 4 | 0 | 0 |
| 4 | Sulphur 37.5% + Pirimicarb 3% SC | 562.5 + 45 | 1500 | 55 | 22 | 17 | 0 | 0 | 62 | 16 | 3 | 0 | 0 |
| 5 | Sulphur 30% + Pirimicarb 2.5% SC | 450 + 37.5 | 1500 | 52 | 37 | 19 | 11 | 21 | 58 | 28 | 23 | 16 | 24 |

TABLE 3-continued

| Treatment | Composition | Active ingredients (grams/hectare) | Formulation Dosage in grams/hectare | Average no. of aphids/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 6 | Sulphur 80% WG | 1250 | 1500 | 48 | 42 | 40 | 40 | 37 | 60 | 15 | 6 | 3 | 0 |
| 7 | Pirimicarb 50% WG | 125 | 250 | 46 | 22 | 12 | 8 | 7 | 47 | 32 | 18 | 16 | 14 |
| 8 | Untreated check | — | — | 62 | 69 | 64 | 70 | 66 | 58 | 60 | 65 | 62 | 70 |

It was observed that the application of Sulphur 60%+Pirimicarb 13% WDG at 900+200 a.i per ha (Treatment 1) was found to be highly effective in controlling the pest population after the $3^{rd}, 7^{th}$ $10^{th}$ and $15^{th}$ days after spraying as compared to individual application of Sulphur 80% WG (Treatment 6) and Pirimicarb 50% WG (Treatment 7) used at a much higher concentration of actives.

It was also found that the combinations of Sulphur+Pirimicarb (Treatments 1 to 5) were highly effective against the mite population in comparison to the individual application of Pirimicarb (Treatment 7) at a higher concentration.

It was also noticed that the SC formulation of Sulphur 37.5%+Pirimicarb 3% SC at 562.5+45 g.a.i. per ha (Treatment 4) showed a good efficacy over the population of aphids and mites and an enhanced control of the pest population for a longer period of time, as compared to Treatment 6 and Treatment 7 with individual actives at higher concentrations.

Further, the presence of sulphur exhibited an enhanced flowering and boll formation as compared to the treatment with individual actives.

Example 4

Bioefficacy of Sulphur+Buprofezin

The trials were carried out in the Rajkot district of Gujarat in India on Bt cotton, CV Vikram-5 following a Randomized block design with four replications and ten treatments with a plot size of 3.6×6.0 m. The spacing followed was 0.9×0.6 m. between rows and plants, respectively. All the agronomic practices were adopted as per recommendations.

The treatments were carried out with after a sufficient population of mealy bugs was developed on the plants after 40-45 days of planting. Five plants were selected randomly in each plot and tagged. On each plant, three twigs (each 10 cm. long) selected randomly were observed critically using magnifying lens for the mites and the number of mealy bugs and mites were counted before as well as after the $3^{rd}, 7^{th}$ $10^{th}$ and $15^{th}$ days of each spraying.

The treatments included combinations of Sulphur plus Buprofezin with varying concentration of the active ingredients, Sulphur 80% WG stand alone and Buprofezin 25% SC stand alone use as standards for comparison along with an untreated control.

The treatments were applied were as indicated in the table below:
Table 4:

| Treatments | Composition | Active ingredients (grams/hectare) | Formulation Dosage in grams/hectare | Average no. of mealy bug/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 40% + Buprofezin 25% WDG | 600 + 375 | 1500 | 57 | 28 | 10 | 4 | 1 | 56 | 40 | 12 | 5 | 4 |
| 2 | Sulphur 50% + Buprofezin 17% WDG | 750 + 255 | 1500 | 62 | 38 | 13 | 7 | 3 | 49 | 37 | 14 | 6 | 2 |
| 3 | Sulphur 60% + Buprofezin 14% WDG | 900 + 210 | 1500 | 68 | 20 | 3 | 0 | 0 | 55 | 10 | 4 | 0 | 0 |
| 4 | Sulphur 70% + Buprofezin 12 WDG | 1050 + 180 | 1500 | 72 | 25 | 7 | 2 | 0 | 69 | 18 | 8 | 3 | 0 |
| 5 | Sulphur 75% + Buprofezin 10% WDG | 1125 + 150 | 1500 | 60 | 28 | 12 | 5 | 2 | 49 | 12 | 4 | 0 | 0 |
| 6 | Sulphur 37.5 + Buprofezin 7% SC | 562.5 + 105 | 1500 | 55 | 22 | 4 | 0 | 0 | 62 | 16 | 3 | 0 | 0 |

-continued

| Treatments | Composition | Active ingredients (grams/hectare) | Formulation Dosage in grams/hectare | Average no. of mealy bug/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 7 | Sulphur 30% + Buprofezin 5% SC | 450 + 75 | 1500 | 58 | 32 | 12 | 8 | 3 | 62 | 22 | 9 | 5 | 3 |
| 8 | Sulphur 80% WG | 1250 | 1500 | 48 | 40 | 38 | 40 | 37 | 60 | 15 | 6 | 3 | 0 |
| 9 | Buprofezin 25% SC | 250 | 1000 | 46 | 23 | 7 | 3 | 0 | 47 | 32 | 18 | 9 | 11 |
| 10 | Untreated check | — | — | 62 | 69 | 64 | 70 | 66 | 58 | 60 | 65 | 62 | 70 |

It was observed that application of Sulphur 60%+Buprofezin 14% WDG at 900+210 g.a.i. per ha (Treatment 3) proved to be effective by providing sufficient and good control over mealy bugs as well as the mite after the $3^{rd}, 7^{th}, 10^{th}$ and $15^{th}$ days of each spraying at reduced concentration of the active ingredients as compared to individual application of Sulphur 80% WG (Treatment 8) and Buprofezin 25% SC (Treatment 9) used at a much higher concentration of actives thus indicating the synergistic effect in managing the mite population.

It was found that Sulphur 70%+Buprofezin 12 WDG at 1050+180 g.a.i. per ha (Treatment 4) and Sulphur 75%+Buprofezin 10 WDG at 1125+150 g.a.i. per ha (Treatment 5) provide an increased control as compared to Buprofezin 25% SC standalone treatment (Treatment 9) at a higher concentration of the active ingredients.

It was also observed that the SC formulation of Sulphur 37.5%+Buprofezin 7% SC at 562.5+105 g.a.i per hectare (Treatment 6) exhibited a better efficacy over the population of mealy bugs and mites as compared to Treatment 8 and Treatment 9 with individual actives at higher concentrations.

The presence of sulphur in the composition exhibited crops with an improved foliage (more greenish leaves and a clearly opened leaf lamina), thus helping in maximizing square formation and retention of flowers at a critical stage and ultimately leading to high yields.

Example 5

Bioefficacy of Sulphur+Thiacloprid

The field experiments were carried out on Cotton in the Akola district of Maharashtra state in India. The experiments were configured with eight treatments which were replicated four times. Cotton hybrid RCH-2Bt was sown in a plot size of 5.4×5.4 sq.m with a spacing of 90×60 cm. The crop was raised following all standard agronomical practices in Randomized Block Design conditions.

The populations of sucking pests viz., thrips, aphids and leafhoppers were recorded from randomly selected ten plants. A day before the imposition of treatment, populations of sucking pest were found to be quite uniform and above the economic threshold level.

The treatments included combinations of Sulphur+thiacloprid with varying concentration of the active ingredients, Sulphur 80% WG stand alone and Thiacloprid 50% WG stand alone use as standards for comparison along with an untreated control. The treatments were applied as indicated in the table below:

TABLE 5

| Treatments | Composition | Active ingredients (grams/hectare) | Formulation Dosage in grams/hectare | Day Before spray | No. of thrips/3 leaves | No. of Jassid/3 leaves | No. of Aphids/3 leaves | No. of mites/3 leaves | No. of Predator/plant |
|---|---|---|---|---|---|---|---|---|---|
| 1 | Sulphur 60% + Thiacloprid 15% WG | 900 + 225 | 1500 | 40 | 7 | 16 | 3 | 4 | 3 |
| 2 | Sulphur 70% + Thiacloprid 7% WG | 1050 + 105 | 1500 | 41 | 9 | 19 | 7 | 0 | 3 |
| 3 | Sulphur 75% + Thiacloprid 6% WG | 1125 + 90 | 1500 | 45 | 13 | 22 | 6 | 0 | 2 |
| 4 | Sulphur 37.5% + Thiacloprid 4% SC | 562.5 + 60 | 1500 | 43 | 10 | 12 | 4 | 3 | 3 |
| 5 | Sulphur 30% + Thiacloprid 3% SC | 450 + 45 | 1500 | 47 | 19 | 16 | 18 | 5 | 1 |

TABLE 5-continued

| Treatments | Composition | Active ingredients (grams/hectare) | Formulation Dosage in grams/hectare | Day Before spray | No. of thrips/3 leaves | No. of Jassid/3 leaves | No. of Aphids/3 leaves | No. of mites/3 leaves | No. of Predator/plant |
|---|---|---|---|---|---|---|---|---|---|
| 6 | Sulphur 80% WG | 1250 | 1500 | 45 | 34 | 38 | 29 | 8 | 2 |
| 7 | Thiacloprid 50% WG | 125 | 250 | 42 | 14 | 21 | 5 | 17 | 2 |
| 8 | Untreated check | — | — | 45 | 48 | 51 | 50 | 49 | 3 |

It was observed that application of Sulphur 60%+Thiacloprid 15% WG at 900+225 g.a.i per hectare (Treatment 1) proved to be very effective in controlling the sucking pest.

The application of Sulphur 70%+Thiacloprid 7% WG at 1050+105 g.a.i per hectare (Treatment 2) was also very effective in controlling the pest as compared to individual application of Sulphur 80% WG (Treatment 6) and Thiacloprid 50% WG (Treatment 7) used at a much higher concentration of actives, where high damage is observed because of mites.

In case of SC formulation application of Sulphur 37.5%+Thiacloprid 4% SC at 562.5+45 g.a.i per hectare (Treatment 4) showed better efficacy over the population of thrips, aphids, jassid and mites and the better control of pest population for a longer period of time as compared to Treatment 6 and Treatment 7 with individual actives at higher concentrations.

The population of thrips, jassids and aphids was counted after the $5^{th}$ day after spraying and it was found that the compositions containing combinations of Sulphur and Thiacloprid was quite effective over sucking pest complex as compared to the insecticide used alone, thus proving a distinct advantage of managing broader spectrum of sucking pests and mites, simultaneously that occurs in nature, on other crop plants of economical importance including fruits and vegetables.

Example 6

Bioefficacy of Sulphur+Acetamiprid

The trials were carried out in Bhatinda district of Punjab state in India on cotton cultivar RCH-2 following a randomized block design with four replications and nine treatments on a plot size of 3.6×6.0 m. All the agronomic practices were adopted as per recommendations.

The treatments were carried out after development of sufficient population of white fly and mites on plants after 20-25 days of transplanting. Five plants were selected randomly in each plot and tagged. On each plant, three twigs selected randomly were observed critically using magnifying lens (for mites) and the number of white flies and mites were counted before as well as after the $3^{rd}$, $7^{th}$, $10^{th}$ and $15^{th}$ days of spraying.

The treatments included combinations of Sulphur+Acetamiprid with varying concentration of the active ingredients, Sulphur 80% WG stand alone and Acetamiprid 20% SP stand alone use as standards for comparison along with an untreated control. The treatments were applied as indicated in the table below:

TABLE 6

| Treatment | Compositions | Active ingredients (grams/hectare) | Formulation Dosage in grams/hectare | Average no. of white fly/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 70% + Acetamiprid 3% WDG | 1050 + 45 | 1500 | 68 | 20 | 3 | 0 | 0 | 55 | 13 | 6 | 0 | 0 |
| 2 | Sulphur 75% + Acetamiprid 2% WDG | 1125 + 30 | 1500 | 72 | 25 | 7 | 2 | 0 | 69 | 18 | 8 | 3 | 0 |
| 3 | Sulphur 80% + Acetamiprid 1.5% WDG | 1200 + 22.5 | 1500 | 60 | 28 | 20 | 18 | 20 | 49 | 12 | 4 | 0 | 0 |
| 4 | Sulphur 50% + Acetamiprid 0.5% WDG | 750 + 7.5 | 1500 | 51 | 38 | 24 | 33 | 38 | 43 | 21 | 13 | 7 | 12 |
| 5 | Sulphur 40% + Acetamiprid 1.5% SE | 600 + 22.5 | 1500 | 55 | 22 | 20 | 10 | 8 | 62 | 16 | 3 | 0 | 0 |
| 6 | Sulphur 35% + Acetamiprid 0.75% SE | 525 + 11.25 | 1500 | 42 | 18 | 15 | 13 | 13 | 52 | 24 | 13 | 7 | 9 |
| 7 | Sulphur 80% WG | 1250 | 1500 | 48 | 40 | 38 | 40 | 37 | 60 | 15 | 6 | 3 | 0 |
| 8 | Acetamiprid 20% SP | 20 | 100 | 46 | 30 | 15 | 18 | 20 | 47 | 32 | 18 | 9 | 11 |
| 9 | Untreated check | — | — | 62 | 69 | 64 | 70 | 66 | 58 | 60 | 65 | 62 | 70 |

It was observed that the applications of Sulphur 70%+ Acetamiprid 3% WDG at 1050+4 g.a.i per ha (Treatment 1) was found to be very effective in controlling the white fly population and found superior after the $3^{rd}$, 7th $10^{th}$ and $15^{th}$ days of spraying as compared to the individual application of Sulphur 80% WG (Treatment 7) and Acetamiprid 20% SP (Treatment 8). The quick knock down effect of mites was observed significantly in Treatment 1 because of presence of Sulphur in the composition.

It was also noticed that the SE formulation Sulphur 40%+ Acetamiprid 1.5% SC at 600+22.5 g.a.i per ha (Treatment 5) showed a better efficacy over the population of white fly and mites and good control upto the $10^{th}$ day of spraying despite being used at very low dosages of the individual active ingredients, especially Sulphur It was observed that the combination of Sulphur+Acetamiprid, were highly effective against the white flies and mite population as compared to Treatment 7 and Treatment 8 with individual actives at higher concentrations.

Further, the presence of sulphur exhibited an enhanced flowering and boll formation as compared to treatment with individual actives.

Example 7

Bioefficacy of Sulphur+Clothianidin

The trials were carried out in Akola district of Maharashtra state in India on cotton. The experiments were configured with eleven treatments which were replicated four times. Cotton hybrid RCH-2Bt was sown in a plot size of 5.4×5.4 sq.m with a spacing of 90×60 cm. The crop was raised following all standard agronomical practices in Randomized Block Design with eleven treatments which were replicated four times. The treatments were carried out after sizeable population of jassids, thrips, aphids were observed.

The populations of sucking pests viz., thrips, aphids and leafhoppers were recorded from randomly selected ten plants. A day before the imposition of treatment, population of sucking pest was quite uniform and above the economic threshold level.

The treatments included combinations of Sulphur+ Clothianidin with varying concentration of the active ingredients, Sulphur 80% WG stand alone and Clothianidin 50% WG stand alone use as standards for comparison along with an untreated control. The treatments were applied as indicated in the table below.

The below table shows the live pest population after the $10^{th}$ day of spraying and it was observed that the combination of sulphur+clothianidin was effective to give sufficient control upto $15^{th}$ day of spraying.

TABLE 7

| Treatments | Composition | Active ingredients (grams/hectare) | Formulation Dosage in grams/hectare | Day Before spray | No. of thrips/3 leaves | No. of Jassid/3 leaves | No. of Aphids/3 leaves | No. of mites/3 leaves | No. of Predator/plant |
|---|---|---|---|---|---|---|---|---|---|
| 1 | Sulphur 60% + Clothianidin 3% WG | 900 + 45 | 1500 | 52 | 3 | 7 | 0 | 10 | 2 |
| 2 | Sulphur 50% + Clothianidin 2.5% WG | 750 + 37.5 | 1500 | 44 | 4 | 9 | 0 | 13 | 3 |
| 3 | Sulphur 60% + Clothianidin 2% WG | 900 + 30 | 1500 | 40 | 7 | 16 | 2 | 9 | 3 |
| 4 | Sulphur 70% + Clothianidin 1.5% WG | 1050 + 22.5 | 1500 | 41 | 5 | 13 | 0 | 3 | 3 |
| 5 | Sulphur 80% + Clothianidin 1% WG | 1200 + 15 | 1500 | 45 | 13 | 22 | 8 | 7 | 2 |
| 6 | Sulphur 80% + Clothianidin 0.5% WG | 1200 + 7.5 | 1500 | 43 | 15 | 21 | 9 | 5 | 3 |
| 7 | Sulphur 40% + Clothianidin 1.5% SC | 600 + 22.5 | 1500 | 43 | 10 | 19 | 7 | 5 | 2 |
| 8 | Sulphur 25% + Clothianidin 0.25% SC | 375 + 3.75 | 1500 | 43 | 22 | 28 | 13 | 27 | 3 |
| 9 | Sulphur 80% WG | 1200 | 1500 | 45 | 34 | 38 | 29 | 8 | 2 |
| 10 | Clothianidin 50% WDG | 25 | 50 | 42 | 12 | 18 | 4 | 17 | 2 |
| 11 | Untreated check | — | — | 45 | 48 | 51 | 50 | 49 | 3 |

The population of thrips, jassid, aphid and mites (mite population were counted with the help of stereoscopic microscope) and Predator was counted after the 5th day after spraying.

It was found that the application of Sulphur 60%+Clothianidin 3% WG at 900+45 g.a.i. per ha (Treatment 1) was the highly effective in controlling the sucking pest complex. The application of Sulphur 70%+Clothianidin 1.5% WG at 1050+22.5 a.i gm per hectare (Treatment 4) was also found to be good in controlling the sucking pests as compared to the individual application of Sulphur 80% WG (Treatment 9) and Clothianidin 50% WDG (Treatment 10) used at a much higher concentration of actives In the case of SC compositions, it was observed that application of Sulphur 40%+Clothianidin 1.5% SC at 600+22.5 g.a.i per ha (Treatment 7) showed better efficacy over the population of thrip, aphid, jassid and mites and the better control of pest population upto longer period of time as compared to Treatment 9 and Treatment 10 with individual actives at higher concentrations.

All the treatments were proved to be safer for Predators and parasites as the number of Coccinellids (grubs and adults)+ grubs of *Chrysoperla carnea* were found safer in all the treatments.

Example 8

Bioefficacy of Sulphur+Diafenthiuron

The treatments were carried out in Rajkot district of Gujarat state in India on cotton following a randomized block design with four replications and twelve treatments with a plot size of 3.6×6.0 m. All the agronomic practices were adopted as per recommendations.

The treatments were carried out after development of sufficient population of white fly and mites on plants after 20-25 days of sowing. Five plants were selected randomly in each plot and tagged. On each plant, three twigs selected randomly were observed critically using magnifying lens (for mites) and the number of white flies and mites were counted before as well as after the $3^{rd}$, $7^{th}$, $10^{th}$ and $15^{th}$ days of spraying.

The treatments included combinations of Sulphur+Diafenthiuron with varying concentration of the active ingredients, Sulphur 80% WG stand alone and Diafenthiuron 50% WP stand alone use as standards for comparison along with an untreated control. The treatments were applied as indicated in the table below.

TABLE 8

| Treatments | Composition | Active ingredients (grams/hectare) | Formulation Dosage in grams/hectare | Average no. of white fly/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 40% + Diafenthiuron 40% WDG | 600 + 600 | 1500 | 58 | 13 | 4 | 0 | 0 | 56 | 42 | 21 | 20 | 22 |
| 2 | Sulphur 40% + Diafenthiuron 35% WDG | 600 + 525 | 1500 | 51 | 18 | 3 | 0 | 0 | 50 | 38 | 14 | 19 | 24 |
| 3 | Sulphur 55% + Diafenthiuron 30% WDG | 825 + 450 | 1500 | 58 | 32 | 5 | 0 | 0 | 55 | 29 | 12 | 6 | 10 |
| 4 | Sulphur 60% + Diafenthiuron 25% WDG | 900 + 375 | 1500 | 72 | 25 | 7 | 3 | 2 | 69 | 32 | 8 | 3 | 0 |
| 5 | Sulphur 70% + Diafenthiuron 20% WDG | 1050 + 300 | 1500 | 55 | 22 | 15 | 5 | 8 | 62 | 16 | 3 | 0 | 0 |
| 6 | Sulphur 75% + Diafenthiuron 15% WDG | 1125 + 225 | 1500 | 55 | 22 | 15 | 5 | 12 | 62 | 16 | 3 | 0 | 0 |
| 7 | Sulphur 70% + Diafenthiuron 12% WDG | 1050 + 180 | 1500 | 61 | 39 | 30 | 21 | 28 | 53 | 28 | 12 | 7 | 5 |
| 8 | Sulphur 37.5% + Diafenthiuron 17.5% SC | 562.5 + 262.5 | 1500 | 55 | 12 | 4 | 0 | 0 | 52 | 16 | 3 | 0 | 0 |

TABLE 8-continued

| Treatments | Composition | Active ingredients (grams/hectare) | Formulation Dosage in grams/hectare | Average no. of white fly/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 9 | Sulphur 20% + Diafenthiuron 7.5% SC | 300 + 112.5 | 1500 | 55 | 22 | 15 | 18 | 28 | 62 | 16 | 8 | 5 | 10 |
| 10 | Sulphur 80% WG | 1250 | 1500 | 48 | 40 | 38 | 40 | 37 | 60 | 15 | 6 | 3 | 0 |
| 11 | Diafenthiuron 50% WP | 300 | 600 | 46 | 18 | 7 | 4 | 7 | 47 | 32 | 18 | 9 | 11 |
| 12 | Untreated check | — | — | 62 | 69 | 64 | 70 | 66 | 58 | 60 | 65 | 62 | 70 |

It was observed that the applications of Sulphur 55%+Diafenthiuron 30% WDG at 825+450 g.a.i per ha (Treatment 3), Sulphur 60%+Diafenthiuron 25% WDG at 900+375 g.a.i per ha (Treatment 4) and Sulphur 70%+Diafenthiuron 20% WDG at 1050+300 g.a.i per ha (Treatment 5) were found to be highly effective in controlling the white fly population at lower concentration after the $3^{rd}, 7^{th}$ $10^{th}$ and $15^{th}$ days of spraying as compared to the individual application of Sulphur 80% WG (Treatment 10) and Diafenthiuron 50% WP (Treatment 11). s It was also observed that the combination of Sulphur+Diafenthiuron, for e.g. Treatment 6, was highly effective against the mite population for a longer duration as compared to Treatment 10 and Treatment 11 with individual actives at higher concentrations showing the synergy between Sulphur and Diafenthiuron.

It was also noticed that the SC formulation Sulphur 37.5%+Diafenthiuron 17.5% SC at 562.5+262.5 g.a.i per ha (Treatment 8) showed good efficacy over the population of white fly and mites and the better control of pest population upto longer period of time was also observed Further, the presence of sulphur in the composition exhibited an enhanced flowering and boll formation as compared to treatment with individual actives providing the necessary sulphur nutrition.

Example 9

Bioefficacy of Sulphur+Novaluron

The treatments were carried out in Hissar district of Haryana state in India using okra (*Abelmoschus esculentus* Moench) crop following randomized block design with four replications and nine treatments with a plot size of 3.6×6.0 m. All the agronomic practices were adopted as per recommendations.

The treatments were carried out after the first signs of infestations about four weeks after planting, single spray was made after development of sufficient population of shoot and fruit borer, *Earias vitella* and mite, *Tetranychus* spp on plants after 35-45 days of sowing. Five plants were selected randomly in each plot and tagged. On each plant, three twigs selected randomly were observed critically using magnifying lens (for mites) and the number of shoot, fruit bore and mite were counted before as well as after the $3^{rd}, 7^{th}, 10^{th}$ and $15^{th}$ days of spraying. It is also to be noted the live shoot and fruit borer, *Earias vitella* was counted by the activity of pest on the top twig portion, where it causes damage.

The treatments included combinations of Sulphur+Novaluron with varying concentration of the active ingredients, Sulphur 80% WG stand alone and Novaluron 10% EC stand alone use as standards for comparison along with an untreated control. The treatments were applied as indicated in the table below.

TABLE 9

| Treatments | Composition | Active ingredients (grams/hectare) | Formulation Dosage in grams/hectare | Average no. of shoot and fruit borer per row of 25 plant | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 70% + Novaluron 10% WDG | 1050 + 150 | 1500 | 19 | 7 | 0 | 0 | 0 | 50 | 16 | 4 | 1 | 0 |
| 2 | Sulphur 70% + Novaluron 7% WDG | 1050 + 105 | 1500 | 16 | 8 | 3 | 0 | 0 | 55 | 13 | 6 | 2 | 0 |
| 3 | Sulphur 75% + Novaluron 5% WDG | 1125 + 75 | 1500 | 14 | 8 | 3 | 0 | 0 | 69 | 18 | 8 | 3 | 0 |
| 4 | Sulphur 80% + Novaluron 2.5% WDG | 1200 + 37.5 | 1500 | 18 | 9 | 7 | 3 | 2 | 49 | 12 | 6 | 3 | 1 |

TABLE 9-continued

| Treatments | Composition | Active ingredients (grams/hectare) | Formulation Dosage in grams/hectare | Average no. of shoot and fruit borer per row of 25 plant | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 5 | Sulphur 40% + Novaluron 2% SC | 600 + 30 | 1500 | 15 | 5 | 2 | 0 | 0 | 62 | 16 | 7 | 3 | 0 |
| 6 | Sulphur 35% + Novaluron 1.25% SC | 525 + 18.75 | 1500 | 20 | 10 | 7 | 9 | 11 | 54 | 21 | 12 | 8 | 14 |
| 7 | Sulphur 80% WG | 1250 | 1500 | 12 | 10 | 13 | 12 | 15 | 60 | 15 | 6 | 3 | 0 |
| 8 | Novaluron 10% EC | 75 | 750 | 15 | 7 | 7 | 2 | 1 | 47 | 32 | 18 | 9 | 11 |
| 9 | Untreated check | — | — | 10 | 11 | 13 | 15 | 15 | 15 | 18 | 18 | 20 | 20 |

It was observed that the applications of Sulphur 70%+Novaluron 10% WDG at 1050+150 g.a.i per ha (Treatment 1), Sulphur 70%+Novaluron 7% WDG at 1050+105 g.a.i per ha (Treatment 2), Sulphur 75%+Novaluron 5% WDG at 1125+75 g.a.i per ha (Treatment 3) and Sulphur 80%+Novaluron 2.5% WDG at 1200+37.5 g.a.i per ha (Treatment 4) were found most effective in treatment against shoot and fruit borer after the $3^{rd}, 7^{th}, 10^{th}$ and $15^{th}$ days of spraying as compared to the individual application of Sulphur 80% WG (Treatment 7) and Novaluron 10% EC (Treatment 8). In fact, Treatment 3 showed very good control for a longer duration despite using lower amount of active ingredients as compared to the stand alone treatments of the active ingredients (Treatments 7 and 8).

It was also noticed that the SC formulation Sulphur 40%+Novaluron 2% SC at 600+30 g.a.i per ha (Treatment 5) showed good efficacy in treatment against shoot and fruit borer and the better control of pest population up to longer period of time was also observed It was observed that the combination of Sulphur+Novaluron, were highly effective against the mite population as compared to Treatment 8 and Treatment 9 with individual actives at higher concentrations It was also observed that residual impact of combination avoided resurgence in mite population (Treatment 3) after $10^{th}$, $15^{th}$ days after spray. Further, the presence of sulphur exhibited an enhanced flowering and boll formation, increased yield as compared to the treatment with individual actives.

Example 10

Bioefficacy of Sulphur+Flubendiamide

The trials were carried out in Surat district of Gujarat state where commercial okra is grown in India using okra (*Abelmoschus esculentus* Moench) crop following a randomized block design with four replications and nine treatments, including control with a plot size of 3.6×6.0 m. All the agronomic practices were adopted as per recommendations.

The treatments were carried out after the first signs of infestations about four weeks after planting, single spray was made after development of sufficient population of shoot and fruit borer, *Earias vitella* and mite, *Tetranychus* spp on plants after 35-45 days of sowing. Five plants were selected randomly in each plot and tagged. On each plant, three twigs selected randomly were observed critically using magnifying lens (for mites) and the number of shoot, fruit bore and mite were counted before as well as after the $3^{rd}, 7^{th}, 10^{th}$ and $15^{th}$ days of spraying. It is also to be noted, the live shoot and fruit borer, *Earias vitella* was counted by the activity of pest at the top twig portion, where it causes damage.

The treatments included combinations of Sulphur+Flubendiamide with varying concentration of the active ingredients, Sulphur 80% WG stand alone and Flubendiamide 20% WG stand alone use as standards for comparison along with an untreated control. The treatments were applied as indicated in the table below:

TABLE 10

| Treatment | Composition | Active ingredients (grams/hectare) | Formulation Dosage in grams/hectare | Average no. of shoot and fruit borer per row of 25 plant | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 75% + Flubendiamide 6% WDG | 1125 + 90 | 1500 | 21 | 4 | 0 | 0 | 0 | 59 | 14 | 4 | 2 | 0 |
| 2 | Sulphur 60% + Flubendiamide 4% WDG | 900 + 60 | 1500 | 16 | 6 | 2 | 0 | 0 | 55 | 13 | 6 | 2 | 0 |

TABLE 10-continued

| Treatment | Composition | Active ingredients (grams/hectare) | Formulation Dosage in grams/ hectare | Average no. of shoot and fruit borer per row of 25 plant | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 3 | Sulphur 70% + Flubendiamide 3% WDG | 1050 + 45 | 1500 | 14 | 8 | 3 | 0 | 0 | 69 | 18 | 8 | 0 | 0 |
| 4 | Sulphur 80% + Flubendiamide 1% WDG | 1200 + 15 | 1500 | 18 | 9 | 7 | 3 | 2 | 49 | 12 | 6 | 3 | 1 |
| 5 | Sulphur 40% + Flubendiamide 2.5% SC | 600 + 30 | 1500 | 15 | 5 | 2 | 0 | 0 | 62 | 16 | 7 | 3 | 0 |
| 6 | Sulphur 25% + Flubendiamide 1% SC | 375 + 15 | 1500 | 18 | 9 | 6 | 8 | 9 | 62 | 16 | 7 | 3 | 13 |
| 7 | Sulphur 80WG | 1250 | 1500 | 12 | 10 | 13 | 12 | 15 | 60 | 15 | 6 | 3 | 0 |
| 8 | Flubendiamide 20% WG | 50 | 250 | 15 | 6 | 3 | 1 | 0 | 47 | 40 | 18 | 9 | 11 |
| 9 | Untreated check | — | — | 10 | 11 | 13 | 15 | 15 | 15 | 18 | 18 | 20 | 20 |

It was observed that the applications of Sulphur 75%+Flubendiamide 6% WDG at 1125+90 g.a.i per ha (Treatment 1), Sulphur 70%+Flubendiamide 3% WDG at 1050+45 g.a.i per ha (Treatment 3) and Sulphur 60%+Flubendiamide 4% WDG 900+60 g.a.i per ha (Treatment 2) were found to be highly effective in treatment against shoot and fruit borer after the $3^{rd}$, $7^{th}$ $10^{th}$ and $15^{th}$ days of spraying as compared to the individual application of Sulphur 80% WG (Treatment 7) and Flubendiamide 20% EG (Treatment 8). It is to be noted that Treatment 1 and 2 exhibited Powdery mildew infection below economic threshold levels (ETL).

It was also noticed that the SC formulation Sulphur 40%+Flubendiamide 2.5% SC at 600+30 g.a.i per ha (Treatment 5) showed good efficacy in treatment against shoot and fruit borer. A better control of pest population up to longer period of time was also observed, despite using lower quantities of active ingredients (Treatments 3,) as compared to the stand alone treatments at higher dosages (Treatments 7,8). Further, the presence of sulphur exhibited an enhanced flowering and boll formation, as compared to treatment with individual actives, while also controlling powdery mildew.

Example 11

Bioefficacy of Sulphur+Spirotetramat

The field trials were carried out in the Akola district of Maharashtra state in India on cotton and following a randomized block design with four replications and nine treatments with a plot size of 3.6×6.0 m. The varieties viz., Bt cotton, CV Vikram-5, were transplanted in experimental fields. All the agronomic practices were adopted as per recommendations.

The treatments were carried out after a sufficient population of aphids and mites was developed on the plants after 20-25 days of transplanting. Five plants were selected randomly in each plot and tagged. On each plant, three twigs selected randomly were observed critically for the mites and the number of aphids and mites were counted before as well as after the $3^{rd}$, $7^{th}$, $10^{th}$ and the $15^{th}$ days of each spraying.

The treatments included combinations of Sulphur and Spirotetramat with varying concentration of the active ingredients, Sulphur 80% WG stand alone and Spirotetramat 15% OD stand alone use as standards for comparison along with an untreated control. The treatments were applied as indicated in the table below.

TABLE 11

| Treatment | Composition | Active ingredients (grams/ hectare) | Formulation Dosage in grams/ hectare | Average no. of aphids/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 50% + Spirotetramat 13% WDG | 750 + 195 | 1500 | 60 | 22 | 5 | 0 | 0 | 55 | 25 | 18 | 13 | 15 |

TABLE 11-continued

| | | Active ingredients | Formulation Dosage | Average no. of aphids/twig/plant in particular period | | | | | Average no. of mite/twig/plant in particular period | | | | |
|---|---|---|---|---|---|---|---|---|---|---|---|---|---|
| Treatment | Composition | (grams/ hectare) | in grams/ hectare | Before spray | 3rd DAS | 7th DAS | 10th DAS | 15th DAS | Before spray | 3rd DAS | 7th DAS | 10th DAS | 15th DAS |
| 2 | Sulphur 75% + Spirotetramat 7% WDG | 1125 + 105 | 1500 | 68 | 20 | 3 | 0 | 0 | 58 | 20 | 9 | 5 | 0 |
| 3 | Sulphur 80% + Spirotetramat 4% WDG | 1200 + 60 | 1500 | 72 | 25 | 7 | 0 | 0 | 69 | 15 | 8 | 0 | 0 |
| 4 | Sulphur 80% + Spirotetramat 3% WDG | 1200 + 45 | 1500 | 60 | 28 | 20 | 18 | 20 | 49 | 12 | 4 | 0 | 0 |
| 5 | Sulphur 40% + Spirotetramat 6.5% SC | 600 + 97.5 | 1500 | 55 | 22 | 20 | 10 | 8 | 62 | 16 | 3 | 0 | 0 |
| 6 | Sulphur 25% + Spirotetramat 2% SC | 375 + 30 | 1500 | 55 | 22 | 20 | 10 | 8 | 62 | 16 | 3 | 0 | 0 |
| 7 | Sulphur 80WG | 1250 | 1500 | 48 | 40 | 38 | 40 | 37 | 60 | 15 | 6 | 3 | 0 |
| 8 | Spirotetramat 15% OD | 90 | 600 | 46 | 30 | 12 | 10 | 14 | 47 | 32 | 18 | 9 | 11 |
| 9 | Untreated check | — | — | 62 | 69 | 64 | 70 | 66 | 58 | 60 | 65 | 62 | 70 |

It was observed that the application of Sulphur 75%+Spirotetramat 7% WDG at 1125+105 g.a.i. per ha (Treatment 2) and Sulphur 80%+Spirotetramat 4% WDG at 1200+60 g a.i. per ha (Treatment 3) were highly effective and superior after the $3^{rd}, 7^{th}$ $10^{th}$ and the $15^{th}$ days after spraying in controlling the pest population as compared to the individual application of Sulphur 80% WG (Treatment 7) and Spirotetramat 15% OD (Treatment 8) used at a much higher concentration of actives (particularly observed in Treatment 3).

It was observed that the combination of Sulphur and Spirotetramat, were highly effective against the mite population as compared to Treatment 7 and Treatment 8 with individual actives at higher concentrations. The knock down effect of mites was visible in Treatment 1, 2 and 3 because of the presence of the sulphur.

It was also observed in the case the SC formulation, that application of Sulphur 40%+Spirotetramat 6.5% SC at 600+97.5 g.a.i per ha (Treatment 5) showed good efficacy in controlling the pest population for longer duration effectively as compared to Treatment 7 and Treatment 8 with individual actives.

Further, the presence of sulphur in the composition exhibited an enhanced flowering and boll formation as compared to treatment with individual actives.

Example 12

Bioefficacy of Sulphur+Thiamethoxam

The trials were carried out in Rajkot district of Gujarat state in India on cotton following a randomized block design with four replications and ten treatments with a plot size of 3.6×6.0 m. The varieties viz., Bt cotton, CV Vikram-5, were transplanted in experimental fields. All the agronomic practices were adopted as per recommendations.

The treatments were carried after development of sufficient populations of aphids and mites on plants after 20-25 days of transplanting. Five plants were selected randomly in each plot and tagged. On each plant, three twigs selected randomly were observed critically using the magnifying lens for mites and the number of aphids and mites were counted before as well as after the $3^{rd}$, $7^{th}$, $10^{th}$ and $15^{th}$ days of after each spraying.

The treatments included combinations of Sulphur+Thiamethoxam with varying concentration of the active ingredients, Sulphur 80% WG stand alone and Thiamethoxam 25% WG stand alone use as standards for comparison along with an untreated control. The treatments were applied as indicated in the table below:

TABLE 12

| Treatments | Compositions | Active ingredients (grams/hectare) Active ingredient | Formulation Dosage in grams/hectare Dosage/ha (gm) | Average no. of aphids/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 50% + Thiamethoxam 5% WDG | 750 + 75 | 1500 | 58 | 14 | 0 | 0 | 0 | 55 | 34 | 11 | 6 | 6 |
| 2 | Sulphur 60% + Thiamethoxam 4% WDG | 900 + 60 | 1500 | 53 | 11 | 4 | 2 | 0 | 50 | 22 | 9 | 4 | 4 |
| 3 | Sulphur 70% + Thiamethoxam 3% WDG | 1050 + 45 | 1500 | 68 | 20 | 3 | 0 | 0 | 55 | 13 | 6 | 2 | 0 |
| 4 | Sulphur 75% + Thiamethoxam 3% WDG | 1125 + 30 | 1500 | 72 | 25 | 7 | 2 | 0 | 69 | 18 | 8 | 0 | 0 |
| 5 | Sulphur 80% + Thiamethoxam 1.5% WDG | 1200 + 22.5 | 1500 | 60 | 28 | 15 | 8 | 20 | 49 | 12 | 4 | 0 | 0 |
| 6 | Sulphur 40% + Thiamethoxam 2.5% SC | 600 + 37.5 | 1500 | 55 | 22 | 8 | 3 | 0 | 62 | 16 | 3 | 0 | 0 |
| 7 | Sulphur 25% + Thiamethoxam 0.67% SC | 375 + 10.05 | 1500 | 50 | 28 | 11 | 15 | 19 | 65 | 24 | 15 | 12 | 10 |
| 8 | Sulphur 80% WG | 1250 | 1500 | 48 | 40 | 38 | 40 | 37 | 60 | 20 | 6 | 3 | 0 |
| 9 | Thiamethoxam 25% WG | 25 | 100 | 46 | 30 | 15 | 18 | 20 | 47 | 32 | 18 | 9 | 11 |
| 10 | Untreated check | — | — | 62 | 69 | 64 | 70 | 66 | 58 | 60 | 65 | 62 | 70 |

It was observed that the applications of Sulphur 70%+Thiamethoxam 3% WDG at 1050+45 g.a.i. per ha (Treatment 3), Sulphur 70%+Thiamethoxam 3% WDG, Sulphur 50%+Thiamethoxam 5% WDG at 750+75 g.a.i. per ha (Treatment 1) and Sulphur 60%+Thiamethoxam 4% WDG at 900+60 g.a.i. per ha (Treatment 2) were most effective and superior after the $3^{rd}, 7^{th}, 10^{th}$ and $15^{th}$ days of spray as compared to the individual application of Sulphur 80% WG (Treatment 8) and Thiamethoxam 25% WG (Treatment 9).

It was also observed that residual impact of combination avoided resurgence in mite population (Treatment 4 and 5) after $10^{th}$, $15^{th}$ days after spray.

All the WDG formulations of, Sulphur+Thiamethoxam at all the four doses (g a. i./ha) was found effective against aphids than the individual application of actives. Thus, Aphids can be effectively managed by spraying of compositions of Sulphur plus Thiamethoxam. The formulations were also found to be safer to the user as well as to the environment.

It was also noticed that the SC formulation of Sulphur 40%+Thiamethoxam 2.5% SC at 600+37.5 g.a.i. per ha (Treatment 6), showed a better efficacy over the population of aphids and mites and a good control of aphids up to the $7^{th}$ day of spraying when compared with the standalone applications of Sulphur 80% WG (Treatment 8) and Thiamethoxam 25% WG (Treatment 9) used at a much higher concentration of actives.

It was observed that the combination of Sulphur+Thiamethoxam were highly effective against the mite population as compared to Treatment 8 with individual application of Sulphur at a higher concentration. Apart from the bio-efficacy, the presence of sulphur in the composition exhibited an enhanced flowering and boll formation in cotton as compared to treatment with individual actives.

Example 13A

Bioefficacy of Sulphur and Imidacloprid

The treatments were carried out in Rajkot district of Gujarat state in India on cotton with combinations of Sulphur and Imidacloprid in varying concentration of active ingredients with Sulphur 80% WG used alone and Imidacloprid 70% WG used alone as standard, along with an untreated control. The treatments were as in the table below.

The treatments were laid out on a randomized block design with four replications and ten treatments with a plot size of 3.6×6.0 m on varieties of Bt cotton, CV Vikram-5. All the agronomic practices were adopted as per recommendations.

The treatments were carried out after development of sufficient population of white fly and mites on plants after 20-25 days of transplanting. Five plants were selected randomly in each plot and tagged. On each plant, three twigs selected randomly were observed critically using magnifying lens (for mites) and the number of jassids and mites were counted before as well as after the $3^{rd}$, $7^{th}$, $10^{th}$ and $15^{th}$ days of spraying.

TABLE 13A

| Treatments | Compositions | Active ingredients (grams/hectare) | Formulation Dosage in grams/hectare | Average no. of jassids/twig/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 70% + Imidacloprid 4% WDG | 1050 + 60 | 1500 | 73 | 20 | 7 | 0 | 0 | 52 | 28 | 7 | 0 | 4 |
| 2 | Sulphur 50% + Imidacloprid 3% WDG | 750 + 45 | 1500 | 60 | 22 | 5 | 0 | 0 | 55 | 34 | 18 | 13 | 15 |
| 3 | Sulphur 60% + Imidacloprid 2% WDG | 900 + 30 | 1500 | 68 | 20 | 3 | 0 | 0 | 58 | 27 | 9 | 5 | 0 |
| 4 | Sulphur 70% + Imidacloprid 1.5% WDG | 1050 + 22.5 | 1500 | 72 | 25 | 7 | 0 | 0 | 69 | 18 | 8 | 0 | 0 |
| 5 | Sulphur 80% + Imidacloprid 1% WDG | 1200 + 15 | 1500 | 60 | 28 | 20 | 18 | 20 | 49 | 12 | 4 | 0 | 0 |
| 6 | Sulphur 40% + Imidacloprid 1.5% SC | 600 + 22.5 | 1500 | 51 | 13 | 7 | 3 | 0 | 56 | 10 | 3 | 0 | 2 |
| 7 | Sulphur 25% + Imidacloprid 0.5% SC | 375 + 7.5 | 1500 | 55 | 22 | 20 | 10 | 8 | 62 | 29 | 15 | 6 | 8 |
| 8 | Sulphur 80% WG | 1250 | 1500 | 48 | 40 | 38 | 40 | 37 | 60 | 15 | 6 | 3 | 0 |
| 9 | Imidacloprid 70% WG | 24.5 | 35 | 46 | 30 | 15 | 10 | 14 | 47 | 32 | 18 | 9 | 11 |
| 10 | Untreated check | — | — | 62 | 69 | 64 | 70 | 66 | 58 | 60 | 65 | 62 | 70 |

The table indicates that application, of first four treatments amongst WDG formulations of Sulphur 70%+Imidacloprid 4% WG at 1050+60 g.a.i. per ha (Treatment 1), Sulphur 50%+Imidacloprid 3% WDG at 750+45 g.a.i. per ha (Treatment 2), Sulphur 60%+Imidacloprid 2% WDG at 900+30 g.a.i. per ha (Treatment 3), and Sulphur 70%+Imidacloprid 1.5% WDG at 1050+22.5 g.a.i. per hectare respectively (Treatment 4) were found highly effective after $3^{rd}, 7^{th}, 10^{th}$ and $15^{th}$ days after spray in controlling jassid populations as compared to individual treatment with sulphur 80% WG (Treatment 8) and Imidacloprid 70% WG (Treatment 9).

It was also observed that the first four treatments of WDG (Treatments 1 to 4) provided control for a longer duration over the jassid populations than the imidacloprid 70% WG (Treatment 9) used alone. Further, the combination of Sulphur 70%+Imidacloprid 1.5% WDG at 1050+22.5 g a.i. per hectare (Treatment 4 and 5) were effective against mite population for longer duration as compared to sulphur 80% WG (Treatment 8) used alone.

In case of SC formulation, Sulphur 40%+Imidacloprid 1.5% SC at 600+22.5 g a.i per hectare (Treatment 6) was found superior in controlling the pest population of jassid as well as mite effectively for longer duration effectively as compared to Treatment 8 and Treatment 9 with individual actives at higher concentrations Further, the presence of sulphur along with imidacloprid exhibited an enhanced flowering and boll formation as compared to treatment with individual actives.

Example 13B

Bioefficacy of Sulphur+Imidacloprid Granule

The trials were conducted on sugarcane in Lucknow district of Uttar Pradesh State in India with six treatments and four replications. The treatments included granular compositions of Sulphur and Imidacloprid in varying concentrations with standalone applications of Sulphur 80% WG used and standalone application of Imidacloprid 70% WG used as standards for comparison, along with an untreated control. The treatments were evaluated against termites on sugarcane.

Each treatment had 25 suckers planted in a row, the whole application of all the treatments was conducted along with sets in the furrows at the time of planting and the same doses were applied at $45^{th}$ DAP. All the agronomic practices were adopted as per recommendations.

The data in the table below represents the cumulative presentation after both the application (at planting and at $45^{th}$ Days after planting)

The germination percentage was noted down in all the treatments and replications:

TABLE 13B

| Treatments | Compositions | Active ingredients (grams/hectare) | Formulation Dosage in grams/hectare | Mean germination percentage after 50th DAP | Yield (ton/ha) |
|---|---|---|---|---|---|
| 1 | Sulphur 90% + Imidacloprid 0.3 Gr. | 13500 + 45 | 15000 | 94 | 108 |
| 2 | Sulphur 80% + Imidacloprid 0.2% Gr. | 12000 + 30 | 15000 | 92 | 103 |
| 3 | Sulphur 70% + Imidacloprid 0.35% Gr. | 10500 + 52 | 15000 | 98 | 110 |
| 4 | Sulphur 60% + Imidacloprid 0.1% Gr. | 9000 + 15 | 15000 | 88 | 100 |
| 5 | Sulphur 50% + Imidacloprid 0.1% Gr. | 7500 + 15 | 15000 | 84 | 98 |
| 6 | Sulphur 90% WG | 6750 | 7500 | 75 | 87 |
| 7 | Imidacloprid 70% WS | 70-105 | 100-150 gm per 100 kg sets | 80 | 92 |
| 8 | Untreated check | — | — | 60 | 70 |

It was observed that the application of Sulphur 70%+Imidacloprid 0.35% Gr.at 10500+52 g.a.i. per ha (Treatment 3) proved to be highly effective with 98 percent of successful germination at the $50^{th}$ day after planting and the least percentage of termite attack and also resulted in a high yield. It was noticed that on application of Sulphur 90%+Imidacloprid 0.3% at 13500+30 g.a.i. per ha (Treatment 1) gave 94 percent germination and high yield. The above treatments were highly efficacious as compared to the individual application of Sulphur 80% WG (Treatment 6) and Imidacloprid 70% WS (Treatment 7) applied at a higher concentration of actives.

The sulphur when combined with Imidacloprid, not only provided an effective control over termites but also displayed an increase in the thickness of the sugarcane stem. Besides the internodes length and eventually the height of the cane was significantly improved when compared with the treatment where sulphur was not used.

The combination of sulphur and Imidacloprid in the composition also demonstrated various other benefits such as increase in the girth, height, internode lengths and thickness of the cane as compared to the observations with the use of imidacloprid alone.

The above composition in practice serves the purpose of simultaneously managing the damage caused by termites found in same medium (soil) and meeting the need of sulphur fertilizer required in the initial stages of plant growth. The composition is thereby rendered highly economical and beneficial to the end-users when compared to the standalone compositions of Imidacloprid or sulphur. The above composition also restricts the undue loading of a carrier such as sand which is present up to a large extent in standalone Imidacloprid compositions Example 14

Bioefficacy of Sulphur and Abamectin

The trial were conducted in Akola district of Maharashtra state in India with several treatments on cotton as indicated in the table below including compositions of sulphur plus abamectin at varying concentrations, Sulphur 80% WG standalone and Abamectin 1.9% EC standalone as standards for comparison, along with an untreated control. The treatments were laid out on a randomized block design with thirteen treatments replicated five times.

The treatments were imposed after sufficient build up of red spider mites. The pre and post treatment observations on live red spider mite populations were assessed on 2, 5, 7 and 10 days after spray.

The treatments were as illustrated in the table below:

TABLE 14

| Treatment | Composition | Active ingredients (grams/hectare) | Formulation Dosage in grams/hectare | Mortality(%) of red spider mite, T. macfarlanei after 5th DAS | Live Mite population at 12th days after spray (in percentage) |
|---|---|---|---|---|---|
| 1 | Sulphur 70% + Abamectin 3% WDG | 1050 + 45 | 1500 | 92 | Nill |
| 2 | Sulphur 65% + Abamectin 2% WDG | 975 + 30 | 1500 | 85 | Nill |

TABLE 14-continued

| Treatment | Composition | Active ingredients (grams/hectare) | Formulation Dosage in grams/hectare | Mortality(%) of red spider mite, T. macfarlanei after 5th DAS | Live Mite population at 12th days after spray (in percentage) |
|---|---|---|---|---|---|
| 3 | Sulphur 65% + Abamectin 1.5% WDG | 975 + 22.5 | 1500 | 76 | 4 |
| 4 | Sulphur 80% + Abamectin 1.5% WDG | 1200 + 22.5 | 1500 | 75 | 2 |
| 5 | Sulphur 85% + Abamectin 1% WDG | 1275 + 15 | 1500 | 66 | 7 |
| 6 | Sulphur 90% + Abamectin 0.5% WDG | 1350 + 7.5 | 1500 | 58 | 13 |
| 7 | Sulphur 90% + Abamectin 0.2% WDG | 1350 + 3.0 | 1500 | 50 | 16 |
| 8 | Sulphur 90% + Abamectin 0.08% WDG | 1350 + 1.2 | 1500 | 48 | 23 |
| 9 | Sulphur 40% + Abamectin 1.5% SC | 600 + 22.5 | 1500 | 88 | Nill |
| 10 | Sulphur 32.5% + Abamectin 0.75% SC | 487.5 + 11.25 | 1500 | 68 | 9 |
| 11 | Abamectin 1.9% EC | 10 | 533 | 63 | 7 |
| 12 | Sulphur 80% WG | 1250 | 1500 | 70 | 8 |
| 13 | Untreated control | — | — | Nill | 38 |

The table indicates that application, of Sulphur 70%+Abamectin 3% WDG at 1050+45 g a.i per hectare (Treatment 1) and Sulphur 65%+Abamectin 2% WDG at 975+30 g a.i per hectare (Treatment 2) proved to be very effective in controlling the red spider mites on leaf area in comparison to the standard Abamectin 1.9% EC at 10 g a.i (Treatment 11) used alone.

The other two compositions of Sulphur 65%+Abamectin 1.5% WDG at 975+22.5 g a.i per hectare and Sulphur 80%+Abamectin 1.5% WDG 1200+22.5 g a.i. per hectare (Treatment 3, 4), were also found superior in controlling red spider mites than Abamectin 1.9% EC at 10 g a.i (Treatment 11) used alone and Sulphur 80% WG at 1250 g a.i. per ha (Treatment 12) used alone It was also observed that residual impact of combination avoided resurgence in mite population after $12^{th}$ days of application.

In case of SC formulations, the application of Sulphur 40%+Abamectin 1.5% SC at 600+22.5 g a.i. per ha (Treatment 9) proved highly effective in reducing the mite population effectively as compared to the individual application with Sulphur 80% WG at 1250 g a.i. per ha (Treatment 12).

It was also observed that with application, of Sulphur 70%+Abamectin 3% WDG at 1050+45 g a.i per hectare (Treatment 1) and Sulphur 65%+Abamectin 2% WDG at 975+30 g a.i per hectare (Treatment 2) and Sulphur 65%+Abamectin 1.5% WDG at 975+22.5 g a.i per hectare (Treatment 3) highest crop yield of 250 quintal, 245 quintal and 230 quintal each per ha was recorded in comparison with the application of Abamectin 1.9% EC at 10 g a.i per hectare (Treatment 11) and Sulphur 80% WG at 1250 g a.i. per hectare (Treatment 12), wherein the yield was found to be 220 quintal & 210 quintals respectively. Thus composition of sulphur and abamectin gave an increased yield of 10 quintals on an average as compared to the stand alone application of the active ingredients.

Example 15

Bioefficacy of Sulphur and Lambda Cyhalothrin

The trials were conducted in Rajkot district of Gujarat state in India on okra (*Abelmoschus esculentus* Moench) crop following a randomized block design with four replications and twelve treatments on a plot size of 3.6×6.0 m. All the agronomic practices were adopted as per recommendations.

The treatments were carried out after the first signs of infestations about four weeks after planting with the treatment being carried out after development of sufficient population of shoot and fruit borer, *Earias vitella* and mite, *Tetranychus* spp on plants after 35-45 days of sowing. Five plants were selected randomly in each plot and tagged. On each plant, three twigs selected randomly were observed critically for mites and the number of shoot borer, fruit borer and mites were counted before as well as after the $3^{rd}$, $7^{th}$, $10^{th}$ and $15^{th}$ days of spraying. It is to be noted, that the live shoot and fruit borer, *Earias vitella* was counted by the activity of pest at the top twig portion, where it causes damage.

The treatments included combinations of Sulphur+Lambda cyhalothrin with varying concentration of the active ingredients, Sulphur 80% WG stand alone and Lambda cyhalothrin 5% EC stand alone use as standards for comparison along with an untreated control. The treatments were applied as indicated in the table below.

TABLE 15

| Treatment | Compositions | Active ingredients (grams/hectare) | Formulation Dosage in grams/hectare | Average no. of shoot and fruit borer/plant in particular period | | | | | Average no. of mite/twig/plant in particular period | | | | |
|---|---|---|---|---|---|---|---|---|---|---|---|---|---|
| | | | | Before spray | 3rd DAS | 7th DAS | 10th DAS | 15th DAS | Before spray | 3rd DAS | 7th DAS | 10th DAS | 15th DAS |
| 1 | Sulphur 70% + Lambda cyhalothrin 4% WP | 1050 + 60 | 1500 | 19 | 6 | 0 | 0 | 0 | 57 | 14 | 3 | 0 | 0 |
| 2 | Sulphur 40% + Lambda cyhalothrin 2% WP | 600 + 30 | 1500 | 21 | 13 | 3 | 0 | 0 | 52 | 28 | 7 | 0 | 4 |
| 3 | Sulphur 50% + Lambda cyhalothrin 2.5% WP | 750 + 37.5 | 1500 | 23 | 10 | 0 | 0 | 0 | 55 | 20 | 9 | 6 | 4 |
| 4 | Sulphur 60% + Lambda cyhalothrin 2% WP | 900 + 30 | 1500 | 16 | 7 | 3 | 0 | 0 | 58 | 20 | 9 | 5 | 0 |
| 5 | Sulphur 70% + Lambda cyhalothrin 1.5% WP | 1050 + 22.5 | 1500 | 14 | 6 | 3 | 0 | 0 | 69 | 18 | 8 | 0 | 0 |
| 6 | Sulphur 80% + Lambda cyhalothrin 1% WP | 1200 + 15 | 1500 | 18 | 9 | 7 | 3 | 2 | 49 | 12 | 4 | 0 | 0 |
| 7 | Sulphur 90% + Lambda cyhalothrin 0.5% WP | 1350 + 7.5 | 1500 | 21 | 15 | 10 | 7 | 7 | 65 | 12 | 3 | 0 | 0 |
| 8 | Sulphur 80% WG | 1250 | 1500 | 12 | 10 | 13 | 12 | 15 | 60 | 20 | 6 | 3 | 0 |
| 9 | Lambda cyhalothri-n 5% EC | 15 | 300 | 15 | 7 | 4 | 1 | 1 | 47 | 32 | 18 | 9 | 11 |
| 10 | Untreated check | — | — | 10 | 11 | 13 | 17 | 19 | 58 | 60 | 65 | 62 | 70 |

It was observed that the applications of Sulphur 70%+Lambda cyhalothrin 4% WDG at 1050+60 g.a.i per ha (Treatment 1), Sulphur 60%+Lambda cyhalothrin 2% WDG at 900+30 g.a.i per ha (Treatment 4), Sulphur 70%+Lambda cyhalothrin 1.5% WDG 1050+22.5 g.a.i per ha (Treatment 5) and Sulphur 80%+Lambda cyhalothrin 1% WDG at 1200+15 g.a.i per ha (Treatment 6) were found to be very effective against the shoot and fruit borer infestation after the $3^{rd}, 7^{th}$ $10^{th}$ and $15^{th}$ days of spraying as compared to the individual application of Sulphur 80% WG (Treatment 8) and Lambda cyhalothrin 5% EC (Treatment 9).

It was observed that the combinations of Sulphur+Lambda cyhalothrin, were also superior effective against the mite population for a longer duration as compared to Treatment 8 and Treatment 9 with individual actives at almost similar dosages of application. In particularly Treatment 5 and 6 showed no mite population after $10^{th}$ and $15^{th}$ days after spray.

Further, the presence of sulphur in the composition exhibited an enhanced flowering and boll formation as compared to treatment with individual actives. The composition also enabled the simultaneous control of various sucking pest complex, such the borer and mites, and helped in more number of pickings.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

We claim:

1. A pesticidal composition comprising sulphur in the range of 20% to 90% w/w of the total composition at least one insecticide selected from the group consisting of pirimicarb in the range of 2.5% to 9% w/w of the total composition, buprofezine in the range of 5% to 25% w/w of the total composition, thiacloprid in the range of 3% to 10% w/w of the total composition, acetamiprid in the range of 0.5% to 5% w/w of the total composition, clothianidin in the range of 0.25% to 3% w/w of the total composition, diafenthiuron in the range of 7.5% to 40% w/w of the total composition, novaluron in the range of 1.25% to 10% w/w of the total composition, flubendiamide in the range of 1% to 6% w/w of the total composition, and spirotetramat in the range of 2% to 13% w/w of the total composition; and at least one agrochemically acceptable excipient.

2. The pesticidal composition of claim 1, wherein the composition is in the form of solid, liquid or a gel.

3. The pesticidal composition of claim 1, wherein the composition is in a form selected from the group consisting of water dispersible granules, suspension concentrates, wettable powders, emulsifiable concentrates, seed dressing, broadcast granules, gels, suspo emulsions, capsulated suspensions, emulsions in water, and oil dispersions.

4. A pesticidal composition in the form of granules comprising elemental sulphur in the range of 50% to 90% w/w of the total composition and imidacloprid or salts thereof in the range of 0.1% to 4% w/w of the total composition and at least one agrochemically acceptable excipient.

5. A pesticidal composition comprising elemental sulphur in the range of 40% to 90% w/w of the total composition, fipronil or salts thereof in the range of 0.3% to 10% w/w of the total composition and at least one agrochemically acceptable excipient.

6. The pesticidal composition of claim 5, wherein the composition is in the form of granules comprising sulphur in the range of 50% to 90% w/w of the total composition and fipronil in the range of 0.3% to 1% w/w of the total composition.

7. A pesticidal composition in the form of wettable powder or granules comprising elemental sulphur in the range of 50% to 90% w/w of the total composition, cartap or salts thereof in the range of 2.25% to 15% w/w of the total composition and at least one agrochemically acceptable excipient.

8. A pesticidal composition comprising elemental sulphur in the range of 30% to 90% w/w of the total composition, lambda-cyhalothrin or salt thereof in the range of 0.35% to 4% w/w of the total composition, and at least one agrochemically acceptable excipient, wherein said composition is a wettable powder (WP), or a combination of encapsulated suspension and suspension concentrate (ZC).

9. A pesticidal composition comprising elemental sulphur in the range of 25% to 80% w/w of the total composition, thiamethoxam or salts thereof in the range of 0.67% to 10% w/w of the total composition, and at least one agrochemically acceptable excipient.

* * * * *